US008946291B2

(12) United States Patent
Hearing et al.

(10) Patent No.: US 8,946,291 B2
(45) Date of Patent: Feb. 3, 2015

(54) COMPOSITIONS AND METHODS FOR TREATING PIGMENTARY CONDITIONS AND MELANOMA

(75) Inventors: Vincent J. Hearing, Leesburg, VA (US); Thierry Passeron, Batiment (FR)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 232 days.

(21) Appl. No.: 13/059,219

(22) PCT Filed: Aug. 15, 2008

(86) PCT No.: PCT/US2008/009762
§ 371 (c)(1),
(2), (4) Date: May 9, 2011

(87) PCT Pub. No.: WO2010/019120
PCT Pub. Date: Feb. 18, 2010

(65) Prior Publication Data
US 2011/0269691 A1  Nov. 3, 2011

(51) Int. Cl.
*A61K 31/203* (2006.01)
*A61K 31/5575* (2006.01)
*A61P 35/00* (2006.01)
*A61K 38/17* (2006.01)

(52) U.S. Cl.
CPC .................................. *A61K 38/1709* (2013.01)
USPC ........................... 514/559; 514/573; 514/19.3

(58) Field of Classification Search
None
See application file for complete search history.

(56) References Cited

U.S. PATENT DOCUMENTS

| 4,342,566 | A | 8/1982 | Theofilopoulos et al. |
| 4,816,567 | A | 3/1989 | Cabilly et al. |
| 4,868,116 | A | 9/1989 | Morgan et al. |
| 4,897,355 | A | 1/1990 | Eppstein et al. |
| 4,980,286 | A | 12/1990 | Morgan et al. |
| 5,006,470 | A * | 4/1991 | Yamaguchi et al. ....... 424/142.1 |
| 5,565,332 | A | 10/1996 | Hoogenboom et al. |
| 5,721,367 | A | 2/1998 | Kay et al. |
| 5,804,440 | A | 9/1998 | Burton et al. |
| 5,837,243 | A | 11/1998 | Deo et al. |
| 5,939,598 | A | 8/1999 | Kucherlapati et al. |
| 6,096,551 | A | 8/2000 | Barbas et al. |
| 6,130,364 | A | 10/2000 | Jakobovits et al. |
| 6,180,377 | B1 | 1/2001 | Morgan et al. |
| 6,261,834 | B1 | 7/2001 | Srivastava |
| 2005/0159485 | A1 * | 7/2005 | Jost-Price et al. ............ 514/559 |

FOREIGN PATENT DOCUMENTS

| EP | 0045665 | 2/1982 |
| WO | WO 89/07136 | 8/1989 |
| WO | WO 90/02806 | 3/1990 |
| WO | WO 94/29348 | 12/1994 |
| WO | WO 2005/102296 | 11/2005 |

OTHER PUBLICATIONS

Bregman et al. Dexamethasone, prostaglandin A, and retinoic acid modulation of murine and human melanoma cells grown in soft agar. J Natl Cancer Inst. Nov. 1983;71(5):927-32.*
Bhuyan et al. Cell cycle effects of prostaglandins A1, A2, and D2 in human and murine melanoma cells in culture. Cancer Res. Apr. 1986;46(4 Pt 1):1688-93.*
Gabor Miklos GL. The human cancer genome project—one more misstep in the war on cancer. Nat Biotechnol. May 2005;23(5):535-7.*
Aberdam et al. (1998) "Involvement of Microphthalmia in the Inhibition of Melanocyte Lineage Differentiation and of Melanogenesis by Agouti Signal Protein" J. Biol. Chem. 273:19560-19565.
Abrahamsen et al. (1991) "Engineering Subtilisin and Its Substrates for Efficient Ligation of Peptide Bonds in Aqueous Solution" Biochemistry 30:4151-4159.
Acsadi et al. (1991) "Human Dystrophin Expression in mdx Mice after Intramuscular Injection of DNA Constructs" Nature 352:815-818.
Afonja et al. (2002) "RAR Agonists Stimulate SOX9 Gene Expression in Breast Cancer Cell Lines: Evidence for a Role in Retinoid-mediated Growth Inhibition" Oncogene 21:7850-7860.
Akiyama et al. (2004) "Interactions between SOX9 and [beta]-catenin Control Chondrocyte Differentiation" Genes Dev. 18:1072-1087.
Akiyama et al. (2004) "Essential Role of SOX9 in the Pathway that Controls Formation of Cardiac Valves and Septa" Proc. Natl. Acad. Sci. USA 101:6502-6507.
Almquist et al. (1980) "Synthesis and Biological Activity of a Ketomethylene Analogue of a Tripeptide Inhibitor of Angiotensin Converting Enzyme" J. Med. Chem. 23:1392-1398.
Anthony-Cahill et al. (1989) "Site-specific Mutagenesis with Unnatural Amino Acids" Trends Biotechnol. 14:400-403.
Arai et al. (2007) "Effects of TS-022, a Newly Developed Prostanoid DP[sub]l Receptor Agonist, on Experimental Pruritus, Cutaneous Barrier Disruptions, and Atopic Dermatitis in Mice" Eur. J. Pharmacol. 556:207-214.
Baggiolini et al. (1992) "Interleukin-8, a Chemotactic and Inflammatory Cytokine" FEBS Lett. 307:97-101.
Bagshawe et al. (1988) "A Cytotoxic Agent Can Be Generated Selectively at Cancer Sites" Br. J. Cancer 58:700-703.

(Continued)

*Primary Examiner* — David Romeo
(74) *Attorney, Agent, or Firm* — Swanson & Bratschun, L.L.C.

(57) ABSTRACT

A method of treating melanoma in a subject comprising administering an amount of SOX9 sufficient to treat melanoma is disclosed. A method of treating a hyperpigmentary condition in a subject comprising administering an amount of inhibitor of SOX9 activity sufficient to treat the condition is disclosed. A method of treating melanoma in a subject comprising administering an amount of SOX9 sufficient to treat melanoma is disclosed. A method of treating melanoma in a subject comprising increasing the amounts of retinoic acid and SOX9 in the subject by amounts sufficient to treat melanoma. A method of treating melanoma in a subject comprising administering an amount of prostaglandin D2 and retinoic acid sufficient to treat cancer is disclosed. A method of sensitizing a melanoma cell to RA comprising administering an amount of SOX9 sufficient to decrease PRAME expression is disclosed.

6 Claims, 5 Drawing Sheets

(56) References Cited

OTHER PUBLICATIONS

Bagshawe (1989) "Towards Generating Cytotoxic Agents at Cancer Sites" Br. J. Cancer 60:275-281.
Battelli et al. (1992) "T Lymphocyte Killing by a Xanthine-oxidase-containing Immunotoxin" Cancer Immunol. Immunother. 35:421-425.
Bell et al. (1997) "SOX9 Directly Regulates the Type-II Collagen Gene" Nature Genetics 16:174-178.
Benner (1994) "Expanding the Genetic Lexicon: Incorporating Non-standard Amino Acids into Proteins by Ribosome-based Synthesis" Trends Biotechnol. 12:158-163.
Berkner et al. (1987) "Abundant Expression of Polyomavirus Middle T Antigen and Dihydrofolate Reductase in an Adenovirus Recombinant" J Virol. 61:1213-1220.
Bertolotto et al. (1996) "Regulation of Tyrosinase Gene Expression by cAMP in B16 Melanoma Cells Involves Two CATGTG Motifs Surrounding the TATA Box: Implication of the Microphthalmia Gene Product" J. Cell Biol. 134:747-755.
Bertolotto et al. (1998) "Microphthalmia Gene Product as a Signal Transducer in cAMP-Induced Differentiation of Melanocytes" J. Cell Biol. 142:827-835.
Bhuyan et al. (1986) "Cell Cycle Effects of Prostaglandins A$_1$, A$_2$, and D$_2$ in Human and Murine Melanoma Cells in Culture" Cancer Res. 46:1688-1693.
Bishop et al. (2000) "A Transgenic Insertion Upstream of SOX9 is Associated with Dominant XX Sex Reversal in the Mouse" Nature Genet. 26:490-494.
Boerner et al. (1991) "Production of Antigen-specific Human Monoclonal Antibodies from In Vitro-Primed Human Splenocytes" J. Immunol 147:86-95.
Bout et al. (1994) "Lung Gene Therapy: In Vivo Adenovirus-mediated Gene Transfer to Rhesus Monkey Airway Epithelium" Human Gene Ther. 5:3-10.
Bowles et al. (2000) "Phylogeny of the SOX Family of Developmental Transcription Factors Based on Sequence and Structural Indicators" Dev. Biol. 227:239-255.
Brigham et al. (1989) "Expression of a Prokaryotic Gene in Cultured Lung Endothelial Cells after Lipofection with a Plasmid Vector" Am. J. Respir. Cell Mol. Biol. 1:95-100.
Brown et al. (1973) "Penetration of Host Cell Membranes by Adenovirus 2" J. Virol. 12:386-396.
Brown et al. (1991) "Molecular and Cellular Mechanisms of Receptor-mediated Endocytosis" DNA Cell Biol. 10:399-409.
Bruggemann et al. (1993) "Designer Mice: The Production of Human Antibody Repertoires in Transgenic Animals" Year Immunol 7.33-40.
Busca et al. (2000) "Cyclic AMP a Key Messenger in the Regulation of Skin Pigmentation" Pigment Cell Res. 13:60-69.
Caillaud et al. (1993) "Adenoviral Vector as a Gene Delivery System into Cultured Rat Neuronal and Glial Cells" Eur. J. Neurosci. 5:1287-1291.
Carrerira et al. (2005) "Mitf Cooperates with Rb1 and Activates p21$^{Cip1}$ Expression to Regulate Cell Cycle Progression" Nature 433:764-769.
Chardonnet et al. (1970) "Early Events in the Interaction of Adenoviruses with HeLa Cells. Penetration of Type 5 and Intracellular Release of the DNA Genome" Virology 40:462-477.
Chen et al. (2006) "Expression of Sex-determining Genes in Human Sebaceous Glands and Their Possible Role in the Pathogenesis of Acne" J. Eur. Acad. Dermatol. Venereol. 20:846-852.
Cheung et al. (2003) "Neural Crest Development is Regulated by the Transcription Factor SOX9" Development 130:5681-5693.
Ciechomska et al. (2005) "Cyclosporine A and Its Non-immunosuppressive Derivative NIM811 Induce Apoptosis of Malignant melanoma Cells in In Vitro and In Vivo Studies" Int. J. Cancer 117:59-67.
Clark-Lewis et al. (1991) "Chemical Synthesis, Purification, and Characterization of Two Inflammatory Proteins, Neutrophil Activating Peptide 1 (Interleukin-8) and Neutrophil Activating Peptide 2" Biochemistry 30:3128-3135.
Clark-Lewis et al. (1994) "Structural Requirements for Interleukin-8 Function Identified by Design of Analogs and CXC Chemokine Hybrids" J. Biol. Chem. 269:16075-16081.
Cole et al. (1985) "The EBV-Hybridoma Technique and Its Application to Human Lung Cancer" Monoclonal Antibodies and Cancer Therapy (Alan R. Liss, Inc.) pp. 77-96.
Cook et al. (2005) "Co-expression of SOX9 and SOX10 during Melanocytic Differentiation In Vitro" Exp. Cell Res. 308:222-235.
Cormier et al. (1997) "Enhancement of Cellular Immunity in Melanoma Patients Immunized with a Peptide from MART-1/Melan a" Cancer J. Sci. Am. 3:37-44.
Cotter et al. (1999) "Molecular Genetic Analysis of Herpesviruses and Their Potential Use as Vectors for Gene Therapy Applications" Curr. Opin. Mol. Ther. 1:633-644.
Creighton (1993) Proteins: Structures and Molecular Properties (WH Freeman) pp. 79-86.
Davidson et al. (1987) "Overproduction of Polyomavirus Middle T Antigen in Mammalian Cells through the Use of Adenovirus Vector" J. Virol. 61:1226-1239.
Dawson et al. (1994) "Synthesis of Proteins by Native Chemical Ligation" Science 266:776-779.
Drivdahl et al. (2004) "Suppression of Growth and Tumorigenicity in the Prostate Tumor Cell Line M12 by Overexpression of the Transcription Factor SOX9" Oncogene 23:4584-4593.
Epping et al. (2005) "The Human Tumor Antigen PRAME Is a Dominant Repressor of Retinoic Acid Receptor Signalling" Cell 122:835-847.
Felgner et al. (1987) "Lipofection: A Highly Efficient, Lipid-mediated DNA-transfection Procedure" Proc. Natl. Acad. Sci. USA 84:7413-7417.
Fitzpatrick et al. (1979) "Prostaglandin D$_2$ Formation by Malignant Melanoma Cells Correlates Inversely with Cellular Metastatic Potential" Proc. Natl. Acad. Sci. USA 76:1765-1769.
Foster et al. (1994) "Campomelic Dysplasia and Autosomal Sex Reversal Caused by Mutations in an SRY-related Gene" Nature 372:525-530.
Furumura et al. (1998) "Characterization of Genes Modulated during Pheomelanogenesis Using Differential Display" Proc. Natl. Acad. Sci. USA 95:7374-7378.
Furumura et al. (2001) Involvement of ITF2 in the Transcriptional Regulation of Melanogenic Genes J. Biol. Chem. 276:28147-28154.
Gaggioli et al. (2003) "Microphtalmia-associated Transcription Factor (MITF) Is Required but Is Not Sufficient to Induce the Expression of Melanogenic Genes" Pigment Cell Res. 16:374-382.
Galibert et al. (2001) "The Usf-1 Transcription Factor is a Novel Target for the Stress-responsive p38 . Kmase and Mediates UV-induced Tyrosinase Expression" EMBO J. 20:5022-5031.
Gomez-Foix et al. (1992) "Adenovirus-mediated Transfer of the Muscle Glycogen Phosphorylase Gene into Hepatocytes Confers Altered Regulation of Glycogen Metabolism" J. Biol. Chem. 267:25129-25134.
Gruber et al. (2005) "The SOX9 Transcription Factor in the Human Disc: Decreased Immunolocalization with Age and Disc Degeneration" Spine 30:625-630.
Guzman et al. (1993) "Efficient Gene Transfer into Myocardium by Direct Injection of Adenovirus Vectors" Circ. Res. 73:1202-1207.
Haj-Ahmad et al. (1986) "Development of a Helper-independent Human Adenovirus Vector and Its Use in the Transfer of the Herpes Simplex Virus Thymidine Kinase Gene" J. Virol. 57:267-274.
Hann et al. (1982) "On the Double Bond Isostere of the Peptide Bond: Preparation of an Enkephalin Analogue" J. Chem. Soc. Perkins Trans. I, pp. 307-314.
Hedstrand et al. (2001) "The Transcription Factors SOX9 and SOX10 Are Vitiligo Autoantigens in Autoimmune Polyendocrine Syndrome Type I" J. Biol. Chem. 276:35390-35395.
Holladay et al. (1983) "Synthesis of Hydroxyethylene and Ketomethylene Dipeptide Isosteres" Tetrahedron Lett. 24:4401-4404.
Hoogenboom et al. (1992) "Bypassing Immunization. Human Antibodies from Synthetic Repertoires of Germline V$_H$ Gene Segments Rearranged In Vitro" J. Mol. Biol. 227:381-388.
Houlton (2007) "SOX9 Gives UV Protection" Chem. Indust., p. 1.

(56) References Cited

OTHER PUBLICATIONS

Hruby (1982) "Conformational Restrictions of Biologically Active Peptides via Amino Acids Side Chain Groups" Life Sci. 31:189-199.
Huang et al. (2000) "Phosphorylation of SOX9 by Cyclic AMP-dependent Protein Kinase A Enhances SOX9's Ability to Transactivate a Col2a1 Chondrocyte-specific Enhancer" Mol. Cell. Biol. 20:4149-4158.
Huber et al. (2003) "A Tissue-restricted cAMP Transcriptional Response" J. Biol. Chem. 278:45224-45230.
Hudson et al. (1979) "Methionine Enkephalin and Isosteric Analogues" Int. J. Peptide Protein Res. 14:177-185.
Hughes et al. (1989) "Monoclonal Antibody Targeting of Liposomes to Mouse Lung In Vivo" Cancer Res. 49:6214-6220.
Hunt et al. (1995) "Agouti Protein Can Act Independently of Melanocyte-stimulating Hormone to Inhibit Melanogenesis" J. Endocrinol. 147:R1-R4.
Ibba et al. (1994) "Towards Engineering Proteins by Site-directed Incorporation In Vivo of Non-natural Amino Acids" Nature Biotechnol. 12:678-682.
Ibba (1995) "Strategies for In Vitro and In Vivo Translation with Non-natural Amino Acids" Biotechnol. Eng. Rev. 13:197-216.
Ikeda et al. (1997) "Characterization of an Antigen that Is Recognized on a Melanoma Showing Partial HLA Loss by CTL Expressing an NK Inhibitory Receptor" Immunity 6:199-208.
Itakura et al. (1984) "Synthesis and use of Synthetic Oligonucleotides" Ann. Rev. Biochem. 53:323-356.
Jaeger et al. (1989) "Improved Predictions of Secondary Structures for RNA" Proc. Natl. Acad. Sci. USA 86:7706-7710.
Jaeger et al. (1990) "Predicting Optimal and Suboptimal Secondary Structure for RNA" Methods Enzymol. 183:281-306.
Jakobovits et al. (1993) "Germ-line Transmission and Expression of a Human-derived Yeast Artificial Chromosome" Nature 362:255-258.
Jakobovits et al. (1993) "Analysis of Homozygous Mutant Chimeric Mice: Deletion of the Immunoglobulin Heavy-chain Joining Region Blocks B-cell Development and Antibody Production" Proc. Natl. Acad. Sci. USA 90:2551-2555.
Jay et al. (2005) "Expression of the Carcinoembryonic Antigen Gene is Inhibited by SOX9 in Human Colon Carcinoma Cells" Cancer Res. 65:2193-2198.
Jennings-White et al. (1982) "Synthesis of Ketomethylene Analogs of Dipeptides" Tetrahedron Lett. 23:2533-2534.
Jiao et al. (2004) "Direct Interaction of SOX10 with the Promoter of Murine Dopachrome Tautomerase (DCT) and Synergistic Activation of DCT Expression with MITF" Pigment Cell Res. 17:352-362.
Jones et al. (1986) "Replacing the Complementarity-determining Regions in a Human Antibody with Those from a Mouse" Nature 321:522-525.
Kawakami et al. (1994) "Cloning of the Gene Coding for a Shared Human Melanoma Antigen Recognized by Autologous T Cells Infiltrating into Tumor" Proc. Natl. Acad. Sci. USA 91:3515-3519.
Kirshenbaum et al. (1993) "Highly Efficient Gene Transfer into Adult Ventricular Mycotes by Recombinant Adenovirus" J. Clin. Invest. 92:381-387.
Kohler et al. (1975) "Continuous Cultures of Fused Cells Secreting Antibody of Predefined Specificity" Nature 256:495-497.
Kwok et al. (1995) "Mutations in SOX9, the Gene Responsible for Campomelic Dysplasia and Autosomal Sex Reversal" Am. J. Hum. Genet. 57:1028-1036.
Kwon et al. (1991) "A Melanocyte-specific Gene, Pmel 17, Maps Near the Silver Coat Color Locus on Mouse Chromosome 10 and Is in a Syntenic Region on Human Chromosome 12" Proc. Natl. Acad. Sci. USA 88:9228-9232.
Larribere et al. (2005) "The Cleavage of Microphthalmia-associated Transcription Factor, MITF, by Caspases Plays an Essential Role in Melanocyte and Melanoma Cell Apoptosis" Genes Dev. 19:1980-1985.
Larue et al. (2006) "The WNT/Beta-catenin Pathway in Melanoma" Front. Biosci. 11:733-742.
La Salle et al. (1993) "An Adenovirus Vector for Gene Transfer into Neurons and Glia in the Brain" Science 259:988-990.
Lee et al. (2000) "Direct Regulation of the Microphthalmia Promoter by SOX10 Links Waardenburg-Shah Syndrome (WS4)-associated Hypopigmentation and Deafness to W52" J. Biol. Chem. 275:37978-37983.
Lee et al. (2003) "Effect of Cyclosporin A on Melanogenesis in Cultured Human Melanocytes" Pigment Cell Res. 16:504-508.
Lefebvre et al. (1997) "SOX9 Is a Potent Activator of the Chondrocyte-specific Enhancer of the Pro[alpha]1(II) Collagen Gene" Mol. Cell. Biol. 17:2336-2346.
Letsinger et al. (1989) "Cholesteryl-conjugated Oligonucleotides: Synthesis, Properties, and Activity as Inhibitors of Replication of Human Immunodeficiency Virus in Cell Culture" Proc. Natl. Acad. Sci. USA 86:6553-6556.
Levy et al. (2006) "MITF: Master Regulator of Melanocyte Development and Melanoma Oncogene" Trends Mol. Med. 12:406-414.
Litzinger et al. (1992) "Biodistribution and Immunotargetability of Ganglioside-stabilized Dioleoylphasphatidylethanolamine Liposomes" Biochim. Biophys. Acta 1104:179-187.
Liu et al. (2008) "Histone Deacetylase Inhibitors Induce Growth Arrest, Apoptosis, and Differentiation in Clear Cell Sarcoma Models" Mol. Cancer Ther. 7:1751-1761.
Ludwig et al. (2004) "Melanocyte-specific Expression of Dopachrome Tautomerase Is Dependent on Synergistic Gene Activation by the SOX10 and MITF Transcription Factors" FEBS Lett. 556:236-244.
Malki et al. (2005) "Prostaglandin D2 Induces Nuclear Import of the Sex-determining Factor SOX9 Via Its cAMP-PKA Phosphorylation" EMBO J. 24:1798-1809.
Malki et al. (2007) "Expression and Biological Role of the Prostaglandin D Synthase / SOX9 Pathway in Human Ovarian Cancer Cells" Cancer Lett. 255:182-193.
Malki et al. (2008) "La Prostaglandine D2: Nouveaux Roles dans la Gonade Embryonnaire et Pathologique" Med. Sci. 24:177-185.
Marks et al. (1991) "Bypassing Immunization: Human Antibodies from V-gene Libraries Displayed on Phage" J. Mol. Biol. 222:581-597.
Massie et al. (1986) "Construction of a Helper-free Recombinant Adenovirus that Expresses Polyomavirus Large T Antigen" Mol. Cell. Biol. 6:2872-2883.
Matsumoto et al. (2007) "[Beta]-Cryptoxanthin, a Novel Natural RAR Ligand, Induces ATP-binding Cassette Transporters in Macrophages" Biochem. Pharmacol. 74:256-264.
McClay et al. (1996) "[Delta][super]12-Prostaglandin-J[sub]2 Is Cytotoxic in Human Malignancies and Synergizes with Both Cisplatin and Radiation" Cancer Res. 56:3866-3869.
Mollaaghababa et al. (2003) "The Importance of Having Your SOX on: Role of SOX10 in the Development of Neural Crest-derived Melanocytes and Glia" Oncogene 22:3024-3034.
Morley (1980) "Modulation of the Action of Regulatory Peptides by Structural Modification" Trends. Pharmacol. Sci. 1:463-468.
Morrison et al. (1984) "Chimeric Human Antibody Molecules: Mouse Antigen-binding Domains with Human Constant Region Domains" Proc. Natl. Acad. Sci. USA 81:6851-6855.
Morsy et al. (1993) "Efficient Adenoviral-mediated Ornithine Transcarbamylase Expression in Deficient Mouse and Human Hepatocytes" J. Clin. Invest. 92:1580-1586.
Moullier et al. (1993) "Correction of Lysosomal Storage in the Liver and Spleen of MPS VII Mice by Implantation of Genetically Modified Skin Fibroblasts" Nature Genet. 4:154-159.
Mulligan (1993) "The Basic Science of Gene Therapy" Science 260:926-932.
Mutoh et al. (2006) "Roles of Prostanoids in Colon Carcinogenesis and Their Potential Targeting for Cancer Chemoprevention" Curr. Pharm. Des. 12:2375-2382.
Mutsaga et al. (2004) "Selective Gene Expression in Mangocellular Neurons in Rat Supraoptic Nucleus" J. Neurosci. 24:7174-7185.
Narang et al. (1980) "Chemical Synthesis of Deoxyoligonucleotides by the Modified Triester Method" Methods Enzymol. 65:610-620.
Needleman et al. (1970) "A General Method Applicable to the Search for Similarities in the Amino Acid Sequence of Two Proteins" J. Mol. Biol. 48:443-453.

(56) References Cited

OTHER PUBLICATIONS

Nielsen et al. (1994) "Peptide Nucleic Acid (PNA). A DNA Mimic with a Peptide Backbone" Bioconjugate Chem. 5:3-7.
Niu et al. (2005) "Receptor-related Mechanism of Proliferation Inhibition and Apoptosis Induction of Human Tongue Squamous Cell Line Tca8113 by Retinoids" J. First. Mil. Med. Univ. 25:935-941.
Panda et al. (2001) "The Transcription Factor SOX9 Regulates Cell Cycle and Differentiation Genes in Chondrocytic CFK2 Cells" J. Biol. Chem. 276:41229-41236.
Passeron et al. (2004) "Cyclic AMP Promotes a Peripheral Distribution of Melanosomes and Stimulates Melanophilin/Slac2-a and Actin Association" FASEB J. 18:989-991.
Passeron et al. (2007) "SOX9 is a Key Player in Ultraviolet B-induced Melanocyte Differentiation and Pigmentation" Proc. Natl. Acad. Sci. USA 104:13984-13989.
Passeron et al. (2009) "Upregulation of SOX9 Inhibits the Growth of Human and Mouse Melanomas and Restores Their Sensitivity to Retinoic Acid" J. Clin. Invest. 119:954-963.
Pearson et al. (1988) "Improved Tools for Biological Sequence Comparison" Proc. Natl. Acad. Sci. USA 85:2444-2448.
Peltonen et al. (2005) "Melanoma Cell Lines are Susceptible to Histone Deacetylase Inhibitor TSA Provoked Cell Cycle Arrest and Apoptosis" Pigment Cell Res. 18:196-202.
Pepicelli et al. (1997) "GDNF Induces Branching and Increased Cell Proliferation in the Ureter of the Mouse" Dev. Biol. 192:193-198.
Piera-Velazquez et al. (2007) "Regulation of the Human SOX9 Promoter by Sp1 and CREB" Exp. Cell. Res. 313:1069-1079.
Pietersz et al. (1992) "Antibody Conjugates for the Treatment of Cancer" Immunol Rev. 129:57-80.
Pingault et al. (1998) "SOX10 Mutations in Patients with Waardenburg-Hirschsprung Disease" Nature Genet. 18:171-173.
Pompolo et al. (2001) "Localisation of the SRY-related HMG Box Protein, SOX9, in Rodent Brain" Brain Res. 906:143-148.
Potterf et al. (2001) "Analysis of SOX10 Function in Neural Crest-derived Melanocyte Development: SOX10-dependent Transcriptional Control of Dopachrome Tautomerase" Dev. Biol. 237:245-257.
Presta (1992) "Antibody Engineering" Curr. Opin. Struct. Biol. 2:593-596.
Qin et al. (2004) "Long-range Activation of SOX9 in Odd Sex (Ods) Mice" Hum. Mol. Genet. 13:1213-1218.
Ragot et al. (1993) "Replication-defective Recombinant Adenovirus Expressing the Epstein-Barr Virus (EBV) Envelope Glycoprotein gp340/220 Induces Protective Immunity against EBV-induced Lymphomas in the Cottontop Tamarin" J. Gen. Virol. 74:501-507.
Rajarathnam et al. (1994) "H NMR Studies of Interleukin 8 Analogs: Characterization of the Domains Essential for Function" Biochemistry 33:6623-6630.
Ram et al. (1993) "In Situ Retroviral-mediated Gene Transfer for the Treatment of Brain Tumors in Rats" Cancer Res. 53:83-88.
Rich et al. (1993) "Development and Analysis of Recombinant Adenoviruses for Gene Therapy of Cystic Fibrosis" Hum. Gene. Ther. 4:461-476.
Riechmann et al. (1988) "Reshaping Human Antibodies for Therapy" Nature 332:323-327.
Rizo et al. (1992) "Constrained Peptides: Models of Bioactive Peptides and Protein Substructures" Annu. Rev. Biochem. 61:387-418.
Roessler et al. (1993) "Adenoviral-mediated Gene Transfer to Rabbit Synovium In Vivo" J. Clin. Invest. 92:1085-1092.
Roffler et al. (1991) "Anti-neoplastic Glucuronide Prodrug Treatment of Human Tumor Cells Targeted with a Monoclonal Antibody-enzyme Conjugate" Biochem. Pharmacol. 42:2062-2065.
Rouzaud et al. (2005) "Regulatory Elements of the Melanocortin 1 Receptor" Peptides 26:1858-1870.
Sambrook et al. (1989) Molecular Cloning: A Laboratory Manual, 2d Ed., Cold Spring Harbor Press; Chapter 5.
Sambrook et al. (1989) Molecular Cloning: A Laboratory Manual, 2d Ed., Cold Spring Harbor Press; Chapter 6.

Schnolzer et al. (1992) "Constructing Proteins by Dovetailing Unprotected Synthetic Peptides: Backbone-engineered HIV Protease" Science 256:221-225.
Sekiya et al. (2000) "SOX9 Enhances Aggrecan Gene Promoter / Enhancer Activity and Is Up-regulated by Retinoic Acid in a Cartilage-derived Cell Line, TC6" J. Biol. Chem. 275:10738-10744.
Senter et al. (1991) "Generation of 5-Fluorouracil from 5-Fluorocytosine by Monoclonal Antibody-cytosine Deaminase Conjugates" Bioconj. Chem. 2:447-451.
Senter et al. (1993) "Generation of Cytotoxic Agents by Targeted Enzymes" Bioconj. Chem. 4:3-9.
Seth et al. (1984) "Role of a Low-pH Environment in Adenovirus Enhancement of the Toxicity of a Pseudomonas Exotoxin-epidermal Growth Factor Conjugate" J. Virol. 51:650-655.
Seth et al. (1984) "Evidence that the Penton Base of Adenovirus Is Involved in Potentiation of Toxicity of Pseudomonas Exotoxin Conjugated to Epidermal Growth Factor" Mol. Cell. Biol. 4:1528-1533.
Simmet et al. (1983) "Inhibition of B-16 Melanoma Growth In Vitro by Prostaglandin D[sub]2" Prostaglandins 25:47-54.
Smith et al. (1981) "Comparison of Biosequences" Adv. Appl. Math. 2:482-489.
Spatola (1983) "Peptide Backbone Modifications: A Structure-activity Analysis of Peptides Containing Amide Bond Surrogates, Conformational Constraints, and RELA" Chemistry and Biochemistry of Amino Acids, Peptides, and Proteins; Weinstein, Ed.; Marcel Dekker, New York; Chapter 5.
Spatola et al. (1986) "Structure-activity Relationships of Enkephalins Containing Serially Replaced Thiomethylene Amide Bond Surrogates" Life Sci. 38:1243-1249.
Stringfellow et al. (1979) "Prostaglandin D[sub]2 Controls Pulmonary Metastasis of Malignant Melanoma Cells" Nature 282:76-78.
Sugimoto et al. (2007) "The Anti-pruritic Efficacy of TS-022, a Prostanoid DP[sub]l Receptor Agonist, Is Dependent on the Endogenous Prostaglandin D[sub]2 Level in the Skin of NC/Nga Mice" Eur. J. Pharmacol. 564:196-203.
Sun et al. (1994) "Human Artificial Episomal Chromosomes for Cloning Large DNA Fragments in Human Cells" Nature Genet. 8:33-41.
Suzuki et al. (1997) "Agouti Signaling Protein Inhibits Melanogenesis and the Response of Human Melanocytes to [alpha]-Melanotropin" J. Invest. Dermatol. 108:838-842.
Svensson (1985) "Role of Vesicles during Adenovirus 2 Internalization into HeLa Cells" J. Virol. 55:442-449.
Sviderskaya et al. (2001) "Agouti Signaling Protein and Other Factors Modulating Differentiation and Proliferation of Immortal Melanoblasts" Dev. Dynam. 22:373-379.
Takenaga (1981) "Stimulation by Retinoic Acid of Prostaglandin Production and Its Inhibition by Tumor Promoters in Mouse Myeloid Leukemia Cells" BIOSIS Database Accession No. PREV198273062790.
Thorson et al. (1991) "A Biosynthetic Approach for the Incorporation of Unnatural Amino Acids into Proteins" Methods Mol. Biol. 77:43-73.
Valencia et al. (2006) "Sorting of Pmel17 to Melanosomes through the Plasma Membrane by AP1 and AP2: Evidence for the Polarized Nature of Melanocytes" J. Cell. Sci. 119:1080-1091.
Varga et al. (1991) "Infectious Entry Pathway of Adenovirus Type 2" J. Virol. 65:6061-6070.
Verastegui et al. (2000) "Regulation of the Microphthalmia-associated Transcription Factor Gene by the Waardenburg Syndrome Type 4 Gene, SOX10" J. Biol. Chem. 275:30757-30760.
Verhoeyen et al. (1988) "Reshaping Human Antibodies: Grafting an Antilysozyme Activity" Science 239:1534-1536.
Virador et al. (1999) "A Standardized Protocol for Assessing Regulators of Pigmentation" Analyt. Biochem. 270:207-219.
Virador et al. (2001) "Production of Melanocyte-specific Antibodies to Human Melanosomal Proteins: Expression Patterns in Normal Human Skin and in Cutaneous Pigmented Lesions" Pigment Cell Res. 14:289-297.
Vu-Dac et al. (1996) "Retinoids Increase Human Apolipoprotein A-II Expression through Activation of the Retinoid X Receptor but Not the Retinoic Acid Receptor" Mol. Cell. Biol. 16:3350-3360.

(56) References Cited

OTHER PUBLICATIONS

Wellbrock et al. (2005) "Elevated Expression of MITF Counteracts B-RAF-stimulated Melanocyte and Melanoma Cell Proliferation" J. Cell. Biol. 170:703-708.

Wickham et al. (1993) "Integrins [alpha][sub]v[beta][sub]3 and [alpha][sub]v[beta][sub]5 Promote Adenovirus Internalization but Not Virus Attachment" Cell 73:309-319.

Wolff et al. (1990) "Direct Gene Transfer into Mouse Muscle In Vivo" Science 247:1465-1468.

Yang et al. (2004) "Seeing the Gene Therapy: Application of Gene Gun Technique to Transfect and Decolor Pigmented Rat Skin with Human Agouti Signaling Protein cDNA" Gene Ther. 11:1033-1039.

Yasumoto et al. (2004) "Epitope Mapping of the Melanosomal Matrix Protein gp100 (PMEL17)" J. Biol. Chem. 279:28330-28338.

Zabner et al. (1993) "Adenovirus-mediated Gene Transfer Transiently Corrects the Chloride Transport Defect in Nasal Epithelia of Patients with Cystic Fibrosis" Cell 75:207-216.

Zabner et al. (1994) "Safety and Efficacy of Repetitive Adenovirus-mediated Transfer of CFTR cDNA to Airway Epithelia of Primates and Cotton Rats" Nature Genet. 6:75-83.

Zhang et al. (1993) "Generation and Identification of Recombinant Adenovirus by Liposome-mediated Transfection and PCR Analysis" BioTechniques 15:868-872.

Zoller (1992) "New Recombinant DNA Methodology for Protein Engineering" Curr. Opin. Biotechnol. 3:348-354.

Zuker (1989) "On Finding All Suboptimal Foldings of an RNA Molecule" Science 244:48-52.

Keenan et al. (1991) American Physiological Society 260(Gastrointest. Liver Physiol. 23):G481-G488 "Contrasting effect of $PGE^2$ and $PGD^2$: ion transport in the canine proximal colon".

Lippton et al. (1980) Prostaglandins and Medicine 5:365-373 "Comparative Effects of $PGD_2$ and $PGE_2$ in the Regional Circulation of the Cat".

Spik et al. (2005) J Immunol 174:3703-3708 "Activation of the Prostaglandin $D_2$ Receptor DPS/CRTH2 Increases Allergic Inflammation in Mouse".

Takaoka et al. (2010) Toxicology 268:40-45 "Opposite effects of two thiazolidinediones, ciglitazone and troglitazone, on proteinase-activated receptor-1-triffered prostaglandin $E_2$ release".

Vickery et al. (1979) Prostaglandins and Medicine 2:3-10 "Opposite and Mutually Antagonistic Effects on Uterine Contractility of Two Epimeric Forms of a Synthetic Prostaglandin Analog".

Thu et al. (2010) Cell Death Differ. 17(8):1325-1334 "Prostaglandin $(PG)D_2$ and 15-deozy-$\Delta^{12}$, $^{14}$-$PGJ_2$, but not $PGE_2$, Mediate Shear-Induced Chondrocyte Apoptosis via Protein Kinase A-dependent Regulation of Polo-like Kinases".

\* cited by examiner

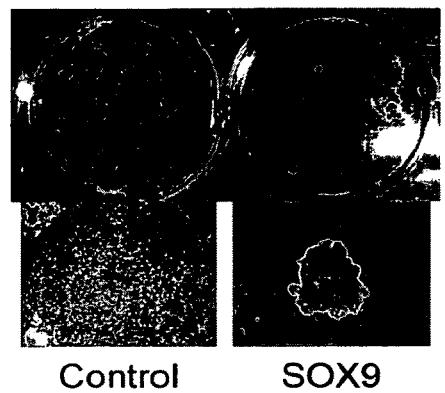 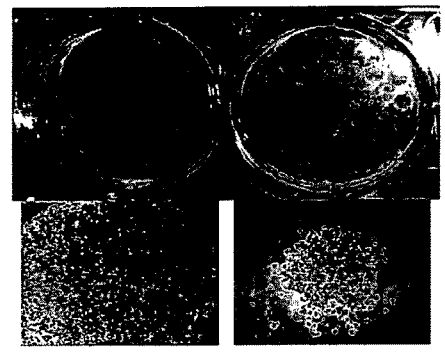
FIG. 1A  FIG. 1B
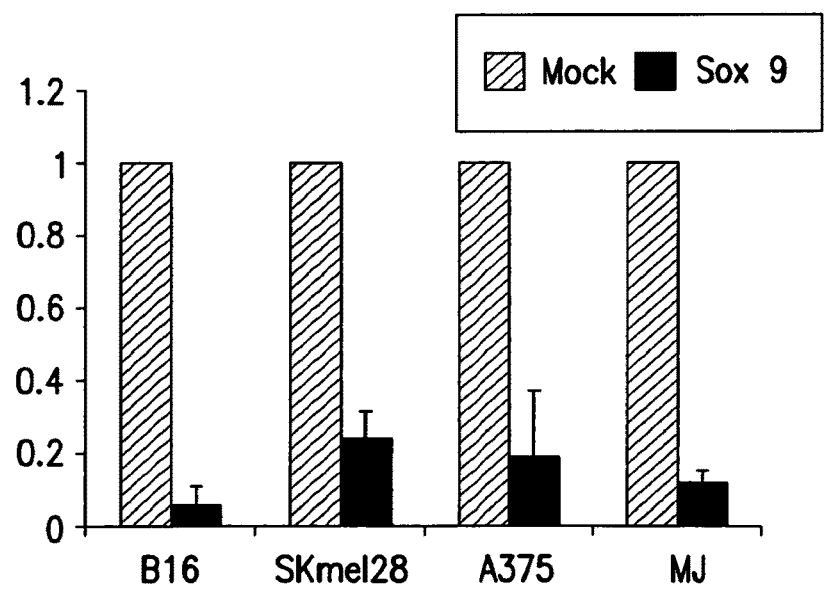
FIG. 1C

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
tgatgtgcca cagttcacaa                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tcctgccagt tttcctgttc                                                   20

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
cctccagtga atcccagaag actct                                             25

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
tgggacaacg ggagtcactc tc                                                22

<210> SEQ ID NO 5
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 5
gggaaggccg cccagggcga                                              20

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
tgccttgccc gactgcagtt ct                                           22

<210> SEQ ID NO 7
<211> LENGTH: 32
<212> TYPE: DNA
<213> ORGANISM: Artificial Sequence
<220> FEATURE:
<223> OTHER INFORMATION: Synthetic

<400> SEQUENCE: 7
atctggcacc acaccttcta caatgagctg cg                                32

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
cgtcatactc ctgcttgctg atccacatct gc                                32

<210> SEQ ID NO 9
<211> LENGTH: 44
<212> TYPE: DNA
<213> ORGANISM: Artificial Sequence
<220> FEATURE:
<223> OTHER INFORMATION: Synthetic

<400> SEQUENCE: 9
catacgattt aggtgacact atagggcag gcggaggcag agga                    44

<210> SEQ ID NO 10
<211> LENGTH: 47
<212> TYPE: DNA
<213> ORGANISM: Artificial Sequence
<220> FEATURE:
<223> OTHER INFORMATION: Synthetic

<400> SEQUENCE: 10
gcgcgtaata cgactcacta tagggctgc tcagctcgcc gatgtcc                 47

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
```
gatgatgtct cctccaaagg                                         20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
agccctacga gtttggtctt                                         20

<210> SEQ ID NO 13
<211> LENGTH: 17
<212> TYPE: DNA
<213> ORGANISM: Artificial Sequence
<220> FEATURE:
<223> OTHER INFORMATION: Synthetic

<400> SEQUENCE: 13
cggtgcgtgc ccagttg                                            17

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
gcgacgcaaa agaagatg                                           18

<210> SEQ ID NO 15
<211> LENGTH: 509
<212> TYPE: PRT
<213> ORGANISM: Artificial Sequence
<220> FEATURE:
<223> OTHER INFORMATION: Synthetic

<400> SEQUENCE: 15

Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
        35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
        115                 120                 125

His Leu His Asn Ala Glu Leu Ser Lys Thr Leu Gly Lys Leu Trp Arg
    130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
            165                 170                 175

Arg Arg Arg Lys Ser Val Lys Asn Gly Gln Ala Glu Ala Glu Glu Ala
        180                 185                 190

Thr Glu Gln Thr His Ile Ser Pro Asn Ala Ile Phe Lys Ala Leu Gln
        195                 200                 205

Ala Asp Ser Pro His Ser Ser Gly Met Ser Glu Val His Ser Pro
    210                 215                 220

Gly Glu His Ser Gly Gln Ser Gln Gly Pro Thr Pro Thr Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
    290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Ser Ala Gly His Val Trp Met
                325                 330                 335

Ser Lys Gln Gln Ala Pro Pro Pro Pro Gln Pro Pro Gln Ala
            340                 345                 350

Pro Pro Ala Pro Gln Ala Pro Pro Gln Pro Ala Ala Pro Pro Gln
            355                 360                 365

Gln Pro Ala Ala Pro Pro Gln Gln Pro Gln Ala His Thr Leu Thr Thr
    370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln His Ser Pro Gln
                405                 410                 415

Gln Ile Ala Tyr Ser Pro Phe Asn Leu Pro His Tyr Ser Pro Ser Tyr
    420                 425                 430

Pro Pro Ile Thr Arg Ser Gln Tyr Asp Tyr Thr Asp His Gln Asn Ser
            435                 440                 445

Ser Ser Tyr Tyr Ser His Ala Ala Gly Gln Gly Thr Gly Leu Tyr Ser
    450                 455                 460

Thr Phe Thr Tyr Met Asn Pro Ala Gln Arg Pro Met Tyr Thr Pro Ile
465                 470                 475                 480

Ala Asp Thr Ser Gly Val Pro Ser Ile Pro Gln Thr His Ser Pro Gln
                485                 490                 495

His Trp Glu Gln Pro Val Tyr Thr Gln Leu Thr Arg Pro
            500                 505

<210> SEQ ID NO 16
<211> LENGTH: 1124
<212> TYPE: DNA
<213> ORGANISM: Artificial Sequence
<220> FEATURE:
<223> OTHER INFORMATION: Synthetic

<400> SEQUENCE: 16
gctcctcctc tccaattcgc ctcccccac ttgtgagcgg gcagctgtga actgtgccac      60
cccgcgcctt cctaatgtgc tcgcctgctg gtagcctggc ctgactgctg ccagcattcc    120

```
cctggtgcgc ctgctatgct ccgaatcctg ggcagccgac ggggagcagg agccacgcgc      180
ctcagagtcc ccgagcccgc cgctggcttc tcgcctattc ccgagacacc atgcccctg      240 ccccgggccc tgcagtatga atctcctgga cccttcatg aagatgacct gactgagcag       300
gagaagggcc tgtcctggcg ccccacagcc ccaccatgtc cgaggactcc gcagggctcg      360
accatgcccg tcgggctccg tgctcggaca ccgagaacac gcggacccag gagaacacgt      420
tccccaaggg cgagcccgat ctgaagaagg agagcgagga cggacaagta tccccgtgtg      480
catccgcgag gcggtcagac aggtgctcaa aggctacgac gtggacgctg gtgcccatgc      540
ctggtagcgt gtcaactggt ccagaaagaa caagcctgac gtcaagcggc ccatgaacgc      600
cttcatggtg tgggcgcagg cggagcgcac gacgctcgcg gaccagtacc cggacttgca      660
caacgccgag ctcagccaga cgctgggcaa gctctggcga ctactgaacg agagcgacga      720
gcgggccttc gtgagcgcag cggccggatg agcggtggct ggtcaccatg aagtgacaca      780
acccgggatt aaacgctacc agaccgcgat aggtaggaac agctgtctca aaatcgtgga      840
cacataggcc ggtcacactg ataggacaca gtgtatgcag agatggagaa gtttatcgcc      900
acacaaggac acattacaac agtagctgga aacgcagact caggccagaa ctaccatcct      960
cccggaattg caccaggcgc tattaccccgt gagaactccc tggagccaag cagcggcccg     1020 cccagaaacac aaacaaagca cacgaaagcc aatgtactcc atcgacggga aataccaacg     1080
aactccacaa tcagcagcga accaccctaa tccccagacg tact                      1124

<210> SEQ ID NO 17
<211> LENGTH: 2214
<212> TYPE: DNA
<213> ORGANISM: Artificial Sequence
<220> FEATURE:
<223> OTHER INFORMATION: Synthetic

<400> SEQUENCE: 17
ctcctcctct ccaattcgcc tccccccact tggagcgggc agctgtgaac tggccacccc       60
gcgccttcct aagtgctcgc cgcggtagcc ggccgacgcg ccagcttccc cgggagccgc      120
ttgctccgca tccgggcagc cgaggggaga ggagcccgcg cctcgagtcc ccgagccgcc      180
gcggcttctc gccttcccg gccaccagcc ccctgccccg gcccgcgta tgaatctcct       240 ggaccccttc atgaagatga ccgacagca ggagaagggc ctgtccggcg cccccagccc      300
caccatgtcc gaggactccg cgggctcgcc ctgcccgtcg ggctccggct cggacaccga     360
gaacacgcgg ccccaggaga cacgttccc caagggcgag cccgatctga agaaggagag      420
cgaggaggac aagttccccg tgtgcatccg cgaggcggtc agccaggtgc tcaaaggcta      480
cgactggacc ctggtgccca tgccggtgcg cgtcaacggc tccagcaaga acaagccgca      540
cgtcaagcgg cccatgaacg ccttcatggt gtgggcgcag gcggcgcgca ggaagctcgc      600
ggaccagtac ccgcacttgc acaacgccga gctcagcaag acgctgggca agctctggag      660
acttctgaac gagagcgaga agcggccctt cgtggaggag gcggagcggc tgcgcgtgca      720
gcacaagaag gaccacccgg attacaagta ccagccgcgg cggaggaagt cggtgaagaa      780
cgggcaggcg gaggcagagg aggccacgga gcagacgcac atctccccca cgccatcttt      840
caaggcgctg caggccgact cgccacactc ctcctccggc atgagcgagg tgcactcccc      900
cggcgagcac tcggggcaat cccagggccc accgacccca ccaccaccc caaaaaccga      960 cgtgcagccg ggcaaggctg acctgaagcg agaggggcgc cccttgccag aggggggcag     1020
```

```
acagccccct atcgacttcc gcgacgtgga catcggcgag ctgagcagcg acgtcatctc   1080
caacatcgag accttcgatg tcaacgagtt tgaccagtac ctgccgccca acggccaccc   1140
gggggtgccg gccacgcacg gccaggtcac ctacacgggc agctacggca tcagcagcac   1200
cgcggccacc ccggcgagcg cgggccacgt gtggatgtcc aagcagcagg cgccgccgcc   1260 accccgcag  cagcccccac aggccccgcc ggccccgcag gcgccccgc  agccgcaggc   1320 ggcgccccca cagcagccgg cggcacccc  gcagcagcca caggcgcaca cgctgaccac   1380
gctgagcagc gagccgggcc agtcccagcg aacgcacatc aagacggagc agctgagccc   1440
cagccactac agcgagcagc agcagcactc gccccaacag atcgcctaca gccccttcaa   1500
cctcccacac tacagccect cctacccgcc catcacccgc tcacagtacg actacaccga   1560
ccaccagaac tccagctcct actacagcca cgcggcaggc cagggcaccg gcctctactc   1620
caccttcacc tacatgaacc ccgctcagcg ccccatgtac accccatcg  ccgacacctc   1680 tggggtccct tccatcccgc agacccacag ccccagcac  tgggaacaac ccgtctacac   1740
acagctcact cgaccttgag gaggcctccc acgaagggcg aagatggccg agatgatcct   1800
aaaaataacc gaagaaagag aggaccaacc agaattccct ttggacattt gtgtttttt    1860 gtttttttat tttgttttgt ttttcttct  tcttcttctt ccttaaagac atttaagcta   1920
aaggcaactc gtacccaaat ttccaagaca caaacatgac ctatccaagc gcattaccca   1980
cttgtggcca atcagtggcc aggccaacct tggctaaatg gagcagcgaa atcaacgaga   2040
aactggactt tttaaaccct cttcagagca agcgtggagg atgatggaga atcgtgtgat   2100
cagtgtgcta aatctctctg cctgtttgga ctttgtaatt attttttag  cagtaattaa   2160 agaaaaaagt cctctgtgag gaatattctc tattttaaaa aaaaaaaaaa aaaa          2214
```

COMPOSITIONS AND METHODS FOR TREATING PIGMENTARY CONDITIONS AND MELANOMA

CROSS-REFERENCE TO RELATED APPLICATIONS

This application is a 35 USC 371 of PCT Application Serial No. PCT/US2008/009762, filed Aug. 15, 2008, currently pending, entitled "SOX9, Prostaglandin D2 and Retinoic Acid for Treating Pigmentary Conditions and Melanoma," which is incorporated herein in its entirety by reference.

FIELD OF THE INVENTION

This invention relates generally to the role of SOX9 in the pigmentation process and in melanoma.

Incorporated by reference herein in its entirety is the Sequence Listing co-submitted with the instant application, entitled "Sequence Listing_ST25_updated.txt", created Feb. 15, 2011, size of 12 kilobytes.

BACKGROUND OF THE INVENTION

Hypopigmentary conditions include vitiligo, and reduced pigmentation due to surgery or other trauma to the skin. Melanocytes are the cells that produce the pigment in the skin and deliver it to the surrounding keratinocytes. Those cells are very fragile and are easily destroyed in case of trauma or surgery (including some laser treatments) leading to hypopigmented scars that can cause psychological discomfort especially in highly pigmented patients. Vitiligo is an acquired cutaneous disorder of pigmentation, with a 0.5% to 2% incidence worldwide, without predilection for sex or race. The clinical presentation is characterized by well circumscribed, white cutaneous macules. Clinical presentation includes segmental vitiligo with a unilateral pattern of the lesions, focal vitiligo characterized by a limited number of depigmented macules without segmental distribution, universal vitiligo which involved complete or almost complete body surface area and generalized vitiligo, the most common type, characterized by a bilateral and symmetrical distribution of the lesions. Individuals affected by vitiligo have a vast reduction of quality of life caused by the colour contrast between healthy pigmented skin and the depigmented vitiligo patches which give the patients psychological problems. Physicians have a large variety of therapeutic approaches (medical (including phototherapy, depigmenting therapies and camouflaging) and surgical) but up to now no treatment provides truly satisfactory results. Other acquired hypopigmentary disorders such as post-surgical leukoderma, are also very frequent and in most cases, remain also challenging to treat.

Hyperpigmentary conditions are very common and come from many origins. Melasma (also called pregnancy mask) is very frequent among young women and is not only related to pregnancy. Its treatment remains challenging especially when the pigment is located in the dermis. Among other types of hyperpigmentation, lentigo senilis (age spots) are also very frequent. Treatment with lasers is effective but remains costly. Other conditions leading to hyperpigmentation are numerous such as freckles, post-inflammatory pigmentation, café-au-lait spots, and acquired brachial pigmentation, just to cite the more frequent.

Melanoma is one of the most deadly cancers. It is generally resistant to radiotherapy and chemotherapy can only provide in the best cases a few additional months of survival. Although used with success in several other cancers, including leukemia or solid cancers such as some breast cancers, retinoic acid (RA) or its derivatives are also ineffective in treating melanoma.

A better understanding of pathways regulating the proliferation of melanoma cells is required to develop efficient strategies to treat this burden on public health. MITF, a transcription factor well known to play a key role in regulating melanogenesis, has been shown to control the proliferation of melanoma cells by directly regulating the p21 promoter (1). Concomitantly it has been shown that MITF acts as an anti-proliferation factor that is down-regulated by B-RAF signaling (2).

SOX9 is a transcription factor that is predominantly reported to be involved in developmental biology. SOX9 has a key role in sexual determination and chondrogenesis and mutations in its encoding gene can lead to campomelic dysplasia and sex reversal (3,4). However there are increasing reports showing the active role of SOX9 in adult tissues such as heart; kidney or brain (5-7).

SUMMARY OF THE INVENTION

In accordance with the purpose(s) of this invention, as embodied and broadly described herein, this invention, in one aspect, relates to methods and compositions for treating melanoma and regulating skin pigmentation or treating pigmentary disorders.

In another aspect, the invention relates to treating PRAME-associated conditions.

In yet another aspect, the invention relates to increasing amounts of SOX9 in an isolated cell or cells in a subject.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiment(s) of the invention and together with the description, serve to explain the principles of the invention.

FIG. 1. SOX9 decreases proliferation of melanoma cells. (A) B16 murine melanoma cells were co-transfected with puromycin resistance vector and either with empty vector (control) or SOX9 cDNA (SOX9) and were grown in medium containing puromycin for 15 d. Upper panels show macroscopic views of the proliferative clones and lower panels the same clones at a magnification of 10×. (B) A375 human melanoma cells were co-transfected with puromycin resistance vector and either with empty vector (control) or SOX9 cDNA (SOX9) and were grown in medium containing puromycin for 15 d. Upper panels show macroscopic views of the proliferative clones and lower panels the same clones at a magnification of 10×. (C) Representation of the relative proliferation of SOX9 transfected cells as compared to control for B16, SKMel28, A375 and Mel Juso (MJ) melanoma cell lines.

DESCRIPTION OF THE PREFERRED EMBODIMENTS

Figure 2A:
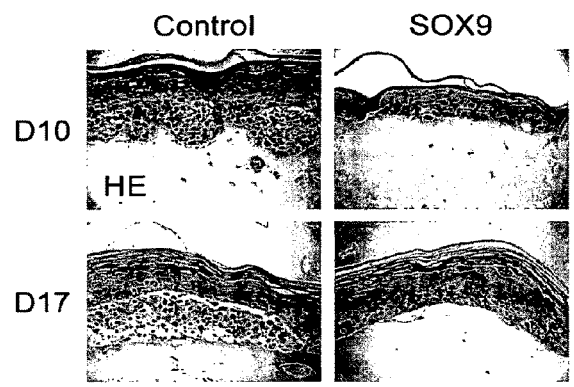
FIG. 2. SOX9 blocks melanoma proliferation in vivo. A375 cells transduced with SOX9 lentivirus or empty lentivirus as a control were included in human reconstructed skin model. (A) Using Hematoxylin Eosin staining, melanoma cells show a clear proliferation at d 10 with some invasiveness of the dermis in the control while no proliferation was noted in A375 cells transduced with SOX9. (B) A375 cells, wild type (WT) or transduced with GFP or SOX9 lentivirus, were injected subcutaneously into nude mice. The graph shows the occurrence of tumors depending on the type of cells from d 7 to d 25. Three photos of mice show examples of the tumorigenicity of A375 cells in nude mice at d 25 (from left to right: A3275 wild-type, a375 GFP, A375 SOX9).

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods or specific compositions as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a melanocyte" includes a culture of melanocytes in vitro or a melanocyte/melanocytes in a melanoma in a subject (in vivo).

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings: "Optional" or "optionally" means that the subsequently described event or circumstance may or may not occur, and that the description includes instances where said event or circumstance occurs and instances where it does not.

The terms "providing," "delivering" and "administering" as used herein refer to any means of adding a compound or molecule to something other than what is being added. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "treating" as used herein refers to administering a compound after the onset of clinical symptoms. Treating may include a partial reduction in symptoms (e.g., a reduction in tumor size or in the number of tumors) or may be a complete cessation of symptoms.

The term "in need of treatment" as used herein refers to a judgment made by a caregiver (e.g. physician, nurse, nurse practitioner, or individual in the case of humans; veterinarian in the case of animals, including non-human mammals) that an individual or animal requires or will benefit from treatment. This judgment is made based on a variety of factors that are in the realm of a care giver's expertise, but that include the knowledge that the individual or animal is ill, or will be ill, as the result of a condition that is treatable by the compounds of the invention. A similar judgment may be mad by a caregiver to determine if a subject (individual) is "in need of prevention."

The terms "individual" and "subject" as used herein refer to a mammal, including animals, preferably mice, rats, other rodents, rabbits, dogs, cats, swine, cattle, sheep, horses, or primates, particularly humans.

The term "non-human animal" refers to any non-human vertebrate, birds and more usually mammals, preferably primates, animals such as swine, goats, sheep, donkeys, horses, cats, dogs, rabbits or rodents, more preferably rats or mice. Both the terms "animal" and "mammal" expressly embrace human subjects unless preceded with the term "non-human".

The terms "higher," "increases," "elevates," or "elevation" refer to increases above basal levels, e.g., as compared to a control. The terms "low," "lower," "reduces," or "reduction" refer to decreases below basal levels; e.g., as compared to a control.

Methods of Treatment

Provided is a method of treating cancer in a subject comprising increasing the activity of SOX9 in the subject by an amount sufficient to treat cancer. It is recognized that the subject being treated is in need of treatment for cancer based, for example, after the patient is diagnosed with cancer. The activity of SOX9 can be increased in the subject by several means, including those described below, each of which is contemplated as a manner of carrying out the invention.

A representative but non-limiting list of cancers that the disclosed methods compositions can be used to treat is the following: lymphoma (Hodgkins and non-Hodgkins), B cell lymphoma, T cell lymphoma, AIDS-related lymphomas, hematopoietic cancers, mycosis fungoides, Hodgkin's Disease, leukemias, myeloid leukemia, myelomas, carcinomas of solid tissues bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers, testicular cancer, colon and rectal cancers, prostatic cancer, or pancreatic cancer, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumors, AIDS-related sarcomas, metastatic cancers, or cancers in general.

In a method of treating cancer comprising increasing the activity of SOX9, the activity can be increased by phosphorylating Sox9 (for example, at Ser 181). This form of SOX9 is effective and is translocated to the nucleus where it has its transcriptional activity. As an example of this method, PGD2 can be administered as it both increases SOX9 expression and phosphorylates it as shown in the Examples.

For example, provided is a method of treating melanoma in a subject comprising administering to the subject an amount of SOX9 sufficient to treat melanoma. The administration can be direct (e.g., delivery of the SOX9 protein to a subject), or it can be indirect (e.g., delivery of a SOX9-expressing nucleic acid construct to the subject or delivery to the subject of a nucleic acid encoding a molecule that increases expression of SOX9).

Thus, in the method of treating melanoma, the SOX9 can be administered directly by intravenous delivery to the subject according to standard IV administration protocols. In some aspects the SOX9 can be administered directly by subcutaneous injection. Further, in other aspects, the SOX9 can be administered directly to a tumor by intratumoral injection.

Alternatively, the SOX9 can be administered by delivery of a lentivirus vector comprising a SOX9 coding sequence. For example, the SOX9 coding sequence can be under the control of a melanocyte-specific promoter.

Alternatively, the SOX9 can be administered by delivery of an adenovirus vector comprising a SOX9 coding sequence. For example, the SOX9 coding sequence can be under the control of a melanocyte-specific promoter. The adenovirus construct can be a commercially available construct, for example the ViraPower™ Adenoviral gateway from Invitrogen (Invitrogen Corporation, Carlsbad, Calif.). This vector achieves stable gene expression at reproducible levels—regardless of mammalian cell type. Using the ViraPower™ Lentiviral System, produces non-replicating viral particles that can efficiently transduce nearly any dividing or non-dividing cell type. In addition, virus-mediated expression allows precise and reproducible control over the number of cells transduced in a population and the number of stably integrated copies of the gene of interest. This allows you expression at the levels needed, in the cells of interest.

Examples of melanocyte-specific promoters that can be used in the methods of expressing SOX9 in vitro or in vivo to treat melanoma or pigmentary conditions include microphthalmia transcription factor (MITF), tyrosinase (TYR), dopachrome tautomerase (DCT), Pmel17 (Kwon et al. (1991) Proc. Natl. Acad. Sci. USA 88, 9228-9232, incorporated herein by reference for its teaching of the promoter pmel17 and its use in expression constructs), or melanoma antigen recognized by T cells 1 (MART-1) (Kawakami et al. (1994) Proc. Natl. Acad. Sci. USA Vol. 91, pp. 3515-3519, and Cormier et al. Enhancement of cellular immunity in melanoma patients immunized with a peptide from MART1/Melan A. *Cancer J.* 3:37-44, 1997 incorporated herein by reference for their teaching of the promoter MART1 and its use in expression constructs).

A further method of treating melanoma in a subject comprises increasing the amounts of retinoic acid (RA) and SOX9 in the subject of by amounts sufficient to treat melanoma. By delivering SOX9 to the subject, expression of PRAME is down-regulated. Decreasing PRAME expression, decreases the resistance of melanoma cells to RA, making RA a useful treatment modality. Thus, in the methods of reducing PRAME, RA can also be administered or activity at the RA receptor increased. Because RA also stimulates expression of SOX9, the restoration of sensitivity of a cell to RA by decreasing PRAME (e.g., through the increase of SOX9 levels) can also restore the increase of SOX9 expression induced by RA, thus creating a positive feed-back scheme. The administration of SOX9 can be direct (e.g., delivery of the SOX9 molecule to a subject), or it can be indirect (e.g., delivery of a SOX9-expressing nucleic acid construct to the subject or delivery to the subject of a nucleic acid encoding a molecule that increases expression of SOX9) as described herein. Similarly, the administration of RA can be direct (e.g., delivery of the RA molecule to a subject), or it can be indirect (e.g., delivery to the subject of a nucleic acid encoding a molecule that is an agonist of the RA receptor (RAR) or delivery to the subject of a nucleic acid encoding a molecule that increases expression of RA) as described herein.

Thus, provided is a method of sensitizing a melanoma cell to RA comprising administering to the subject an amount of SOX9 sufficient to decrease PRAME expression. PRAME expression can be measured according to the methods described herein and elsewhere. The determination of what constitutes an amount of SOX9 sufficient to decrease expression of PRAME is, thus, routine.

A further method of treating melanoma in a subject comprises administering to the subject an amount of prostaglandin D2 (PGD2) and RA sufficient to treat cancer. The RA and PGD2 can be concurrently administered or sequentially administered in either order. The timing of sequential administration is based on the consideration that the SOX9 expression increase caused by administration of PGD2 should be present at the time the RA is administered. Otherwise, the timing of administration for successful treatment can vary. The administration of PDG2 can be direct (e.g., delivery of the PDG2 molecule to a subject), or it can be indirect (e.g., delivery to the subject of a nucleic acid encoding a molecule that increases expression of PGD2 or delivery of a nucleic acid encoding a molecule that is an agonist of the PGD2 receptor) as described herein. Similarly, the administration of RA can be direct (e.g., delivery of the RA molecule to a subject), or it can be indirect (e.g., delivery to the subject of a nucleic acid encoding a molecule that is an agonist of the RA receptor (RAR) or delivery to the subject of a nucleic acid encoding a molecule that increases expression of RA) as described herein.

Provided is a method of decreasing expression of PRAME in a subject comprising administering to the subject an amount of SOX9 sufficient to decrease PRAME expression. By decreasing PRAME expression, a reduction in the resistance of melanoma cells to RA makes RA a useful treatment modality. Furthermore, methods of reducing PRAME expression can include a step of administering of RA or increasing activity at the RA receptor.

Because PRAME is implicated in resistance to RA treatment in a number of cancers, provided are methods of treating cancers that involve PRAME-mediated resistance to RA treatment. For example, methods of treating solid tumors, e.g., neuroblastomas, lung cancer, renal carcinoma are provided, comprising the methods taught herein for reducing PRAME expression. Further examples of the present method include methods of treating other cancers, e.g., carcinomas, carcinomas of solid tissues, squamous cell carcinomas, adenocarcinomas, sarcomas, gliomas, high grade gliomas, blastomas, neuroblastomas, plasmacytomas, histiocytomas, adenomas, hypoxic tumours, myelomas, AIDS-related lymphomas or sarcomas, mycosis fungoides, bladder cancer, brain cancer, nervous system cancer, head and neck cancer, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the of head, neck, mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, testicular cancer; colon and rectal cancers, prostatic cancer, or pancreatic cancer, comprising reducing PRAME-mediated resistance to RA by upregulating SOX9 expression or activity.

Also provided is a method of increasing p21 expression in a subject comprising administering to the subject an amount of SOX9 sufficient to increase p21 expression. The administration can be direct (e.g., delivery of the SOX9 molecule to a subject) as described herein, or it can be indirect (e.g., delivery of a SOX9-expressing nucleic acid construct to the subject or delivery to the subject of a nucleic acid encoding a molecule that increases expression of SOX9) as describe herein.

Further provided is a method of treating a solid tumor (e.g., melanoma) in a subject comprising administering to the subject an amount of a calcineurin inhibitor sufficient to treat melanoma.

The calcineurin inhibitor can be any of the known calcineurin inhibitors. For example, the inhibitors can be selected from the following: NIM811, and others available in the art. A primary consideration in the selection of a calcineurin inhibitor is that it should have minimal immunosuppressive effect. A calcineurin inhibitor without immunomodulatory effects, has recently been developed (23). As evidenced by the teaching of Ciechomska, I., et al. (Cyclosporine A and its non-immunosuppressive derivative NIM811 induce apoptosis of malignant melanoma cells in in vitro and in vivo studies. Int J Cancer 117, 59-67 (2005), incorporated herein by reference for its teaching of this calcineurin inhibitor and its doses), such inhibitors are available and others can be made or identified by similar means.

Provided is a method of treating a solid tumor, (e.g., melanoma) in a subject comprising administering to the subject and amount of DP1 or a DP1 receptor agonist sufficient to treat melanoma. Binding at the DP1 receptor leads to increase expression of SOX9, which in turn treats melanoma. In the method of treating melanoma by a DP1 receptor agonist, the DP1 receptor agonist can be TS-022. TS-022: [{4-[(1R,2S,3R,5R)-5-Chloro-2-((S)-3-cyclohexyl3-hydroxyprop-1-ynyl)-3-hydroxyl-cyclopentyl]butylthio}acetic acid monohydrate is a prostanoid DP1 receptor agonist (M. Sugimoto et al. European Journal of Pharmacology 564 (2007) 196-203, incorporated herein by reference for its teaching of the DP1 receptor agonist). The administration of DP1 can be direct (e.g., delivery of the DP1 molecule to a subject), or it can be indirect (e.g., delivery of a DP1-expressing nucleic acid construct to the subject or delivery to the subject of a nucleic acid encoding a molecule that increases expression of DP1). Delivery of a DP1 receptor agonist can be direct (e.g., delivery of the DP1 agonist molecule to a subject) or it can be indirect (e.g., delivery of a nucleic acid encoding a molecule that is an agonist of the DP1 receptor).

The methods and compositions disclosed herein may also be used for the treatment of precancer conditions and dysplasias that may precede the development of solid cancers.

Because of the discovery of the role of SOX9 in normal pigmentation, a method of treating a hypopigmentary condition in a subject is provided, comprising administering to the subject an amount of SOX9 sufficient to treat the condition. The method of treating a hypopigmentary condition can be carried out using any of the means disclosed herein for increasing the amount of SOX9 in the relevant cells of the subject. The hypopigmentary condition treated by the present methods can be the result of surgery, trauma or vitiligo. For example, the DP1 agonist disclosed herein (TS-022) is delivered to patients with vitiligo using topical dosages in a range as described herein and in the published literature.

Because of the discovery of the role of SOX9 in normal pigmentation, a method of treating a hyperpigmentary condition in a subject is provided, comprising inhibiting SOX9 activity in the subject. The method of treating a hyperpigmentary condition can be carried out using any of the means disclosed herein or known in the art for decreasing SOX9 activity or the amount of SOX9 in the relevant cells of the subject. For example, SOX9 activity can be inhibited by administering to the subject an amount of SOX9 antibody sufficient to treat the condition. SOX9 activity can also be inhibited by administering to the subject an amount of calcineurin (or calcineurin agonist) sufficient to treat the condition. SOX9 activity can further be inhibited by administering to the subject an amount of a SOX9 anti-sense construct sufficient to treat the condition. The hyperpigmentary condition treated by the present methods can be Melasma (also called pregnancy mask), lentigo senilis (age spots), freckles, post-inflammatory pigmentation, café-au-lait spots, and acquired brachial pigmentation. For such methods topical administration of a DP1 antagonist or a calcineurin agonist would be preferred.

In the present methods of treating solid tumors, the SOX9, RA, RAR agonist, PGD2, PGD2 receptor agonist, DP1 or DP1 receptor agonist and combinations thereof can be combined with other cancer therapies. Numerous anti-cancer drugs are available for combination with the present method and compositions. The following are lists of anti-cancer (antineoplastic) drugs that can be used in conjunction with the presently disclosed SOX9 activity-enhancing or expression-enhancing methods.

Antineoplastic: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors;

matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; fas inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Compositions

Provided are compositions of matter for carrying out the methods of the invention. It is recognized that numerous additional compositions can be used to accomplish the steps of the disclosed methods. Thus, the compositions disclosed are exemplary only.

Disclosed are the components to be used to prepare the disclosed compositions, and the compositions themselves to be used within the methods disclosed herein. These and other materials are disclosed herein, and it is understood that when combinations, subsets; interactions, groups, etc. of these materials are disclosed that while specific reference of each individual and collective combinations and permutations of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Provided is a pharmaceutical composition comprising PGD2 and RA, wherein PGD2 is in an amount sufficient to increase SOX9 expression (to reduce PRAME expression), and wherein RA is in an amount sufficient to induce proliferation arrest, differentiation, or apoptosis of cancer cells when combined with a pharmaceutical agent that increases SOX9.

Provided is a pharmaceutical composition comprising a PGD2 receptor agonist and RA, wherein PGD2 receptor agonist is in an amount sufficient to increase SOX9 expression (to reduce PRAME expression), and wherein RA is in an amount sufficient to induce proliferation arrest, differentiation, or apoptosis of cancer cells.

Provided is a pharmaceutical composition comprising DP1 and RA, wherein DP1 is in an amount sufficient to increase SOX9 expression (to reduce PRAME expression), and wherein RA is in an amount sufficient to induce proliferation arrest, differentiation, or apoptosis of cancer cells.

Provided is a pharmaceutical composition comprising DP1 receptor agonist and RA, wherein DP1 receptor agonist is in an amount sufficient to increase SOX9 expression (to reduce PRAME expression), and wherein RA is in an amount sufficient to induce proliferation arrest, differentiation, or apoptosis of cancer cells.

Provided is a pharmaceutical composition comprising SOX9 and RA, wherein SOX9 is in an amount sufficient to reduce PRAME expression (and/or directly inhibit melanoma cell proliferation), and wherein RA is in an amount sufficient to induce proliferation arrest, differentiation, or apoptosis of cancer cells.

In the present methods of treating cancers in which PRAME causes resistance to RA treatment (e.g., melanoma), an RA receptor (RAR) agonist can be administered along with SOX9 or a SOX9-expression enhancing molecule as disclosed herein and in the art. Examples of RAR that can be used in the present methods are disclosed herein and in the art.

Antibodies

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with SOX9 such that SOX9 is inhibited from interacting with MITF. Antibodies that bind the disclosed regions of SOX9 involved in the interaction between SOX9 and MITF are also disclosed. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term-"antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human Antibodies

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86-95, 1991). Human antibodies (and fragments thereof) can also be produced using phage display libraries (Hoogenboom et al., J. Mol. Biol., 227:381, 1991; Marks et al., J. Mol. Biol., 222: 581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255-258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Administration of Antibodies

Administration of the antibodies can be done as disclosed herein. Nucleic acid approaches for antibody delivery also exist. The anti SOX9 antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

Protein

One example of the SOX9 protein is encoded by the SOX9 cDNA sequence disclosed as GENBANK accession number BC007951, and has the following sequence:

(SEQ ID NO: 15)
MNLLDPFMKMTDEQEKGLSGAPSPTMSEDSAGSPCPSGSGSDTENTRPQE

NTFPKGEPDLKKESEEDKFPVCIREAVSQVLKGYDWTLVPMPVRVNGSSK

NKPHVKRPMNAFMVWAQAARRKLADQYPHLHNAELSKTLGKLWRLLNESE

KRPFVEEAERLRVQHKKDHPDYKYQPRRRKSVKNGQAEAEEATEQTHISP

NAIFKALQADSPHSSSGMSEVHSPGEHSGQSQGPPTPPTTPKTDVQPGKA

DLKREGRPLPEGGRQPPIDFRDVDIGELSSDVISNIETFDVNEFDQYLPP

NGHPGVPATHGQVTYTGSYGISSTAATPASAGHVWMSKQQAPPPPQQPP

QAPPAPQAPPQPQAAPPQQPAAPPQQPQAHTLTTLSSEPGQSQRTHIKTE

QLSPSHYSEQQQHSPQQIAYSPFNLPHYSPSYPPITRSQYDYTDHQNSSS

YYSHAAGQGTGLYSTFTYMNPAQRPMYTPIADTSGVPSIPQTHSPQHWEQ

PVYTQLTRP

Other identifying information for the human SOX9 nucleic acid and protein are as follows: ATCC® Number: MGC-14364; I.M.A.G.E. CloneID: 4299305; GenBank Definition Line: SRY (sex determining region Y)-box 9 (campomelic dysplasia, autosomal sex-reversal); Gene Symbol: SOX9; GenBank Numbers: BF688554 & BC007951; LocusID: 6662; UniGene Cluster ID: Hs.2316; Tissue Description: normal pigmented retinal epithelium; Species: *Homo sapiens*; and Vector: pOTB7.

By accessing the GenBank Accession Nos. set forth herein, one of skill in the art can access additional GenBank Accession Nos. listed therein to obtain additional information concerning signal sequences and mature protein sequences. The information provided under the GenBank and ATCC accession numbers, including sequences for SOX9 proteins and nucleic acids (primary amino acid sequence, coding sequences, signal sequence and mature protein residue numbers, primers, etc.) is incorporated herein in its entirety.

Protein Variants

Functional variants of the SOX9 protein and other protein compositions disclosed herein are contemplated. In addition, to the known functional interspecies variants there are derivatives of the SOX9 proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place.

Such substitutions generally are made in accordance with the following Tables 1 and 2 and are referred to as conservative substitutions.

TABLE 1

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions
Original Residue Exemplary Conservative
Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, GENBANK sequence # BF688554 sets forth a particular sequence of SOX9 (i.e., the amino acid sequence encoded by the cDNA for SOX9 shown in the database). Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the SOX9 protein is set forth in GenBank accession no. BF688554.

It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include CH2NH—, —CH2S—, —CH2-CH2-, —CH=CH— (cis and trans), —COCH2-, —CH(OH)CH2-, and —CHH2SO— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH2NH—, CH2CH2-); Spatola et al. Life Sci 38:1243-1249 (1986) (—CHH2-S); Hann J. Chem. Soc Perkin Trans. 1307-314 (1982) (—CH—CH—, cis and trans); Almquist et al. J. Med. Chem. 23:1392-1398 (1980) (—COCH2-); Jennings-White et al. Tetrahedron Lett 23:2533 (1982) (—COCH2-); Szelke et al. European Appln, EP 45665 CA (1982): 97:39405 (1982) (—CH(OH)CH2-); Holladay et al. Tetrahedron. Lett 24:4401-4404 (1983) (—C(OH)CH2-); and Hruby Life Sci 31:189-199 (1982) (—CH2-S—); each of which is incorporated herein by reference. A particularly preferred non-peptide linkage is —CH2NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Screening Methods

Provided is a method of identifying a compound that inhibits melanoma cell proliferation comprising: contacting a melanocyte with the compound; and measuring the amount of SOX9 expression in the contacted melanocyte, an increase in SOX9 expression in the contacted melanocyte compared to SOX9 expression in the absence of the compound indicating a compound that inhibits melanoma cell proliferation. The level of SOX9 expression that is indicative of inhibition of cell proliferation is an amount that is detectable by western blot as shown herein. In most cells SOX9 is not detectable or is detectable at very low levels. As shown herein, a doubling of SOX9 produces a decrease in PRAME. For example, this method could be used to screen for a compound that phosphorylates SOX9 (for example at Ser 181) since this form is effective and is translocated into the nucleus to have its transcriptional activity. PGD2 is identifiable by this method.

Also provided is a method of identifying a compound that inhibits melanoma cell proliferation comprising: contacting a melanocyte with the compound; and measuring the amount of p21 expression in the contacted melanocyte, an increase in p21 expression in the contacted melanocyte compared to p21 expression in the absence of the compound indicating a compound that inhibits melanoma cell proliferation. The level of p21 expression that is indicative of inhibition of cell proliferation is an amount that is detectable by western blot as shown herein. In most cells p21 is not detectable or is detectable at very low levels. This can also be confirmed by cell-growth inhibition assay.

Further provided is a method of identifying a compound that stimulates the DP1 receptor, comprising: contacting a melanocyte with the compound; and measuring the amount of p21 expression in the contacted melanocyte, an increase in p21 expression in the contacted melanocyte compared to p21 expression in the absence of the compound indicating a compound that stimulates the DP1 receptor. The level of p21 expression that is indicative of inhibition of cell proliferation is an amount that is detectable by western blot as shown herein. In most cells p21 is not detectable or is detectable at very low levels.

A method of identifying a melanoma cell susceptible to RA treatment is provided, comprising: measuring the amount of PRAME expression in the melanocyte, a detectable decrease in PRAME expression in the melanocyte indicating that the melanocyte is susceptible to treatment with RA.

Nucleic Acids

There are a variety of molecules disclosed herein that are nucleic acid based, including for example the nucleic acids that encode, for example, SOX9 as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

An example of a nucleic acid encoding a SOX9 protein is disclosed at GenBank accession no. BF688554 and has the following sequence:

(SEQ ID NO: 16)
GCTCCTCCTCTCCAATTCGCCTCCCCCCACTTGTGAGCGGGCAGCTGTGA

ACTGTGCCACCCCGCGCCTTCCTAATGTGCTCGCCTGCTGGTAGCCTGGC

CTGACTGCTGCCAGCATTCCCCTGGTGCGCCTGCTATGCTCCGAATCCTG

GGCAGCCGACGGGGAGCAGGAGCCACGCGCCTCAGAGTCCCCGAGCCCGC

CGCTGGCTTCTCGCCTATTCCCGAGACACCATGCCCCCTGCCCCGGGCCC

TGCAGTATGAATCTCCTGGACCCCTTCATGAAGATGACCTGACTGAGCAG

GAGAAGGGCCTGTCCTGGCGCCCCACAGCCCCACCATGTCCGAGGACTCC

GCAGGGCTCGACCATGCCCGTCGGGCTCCGTGCTCGGACACCGAGAACAC

GCGGACCCAGGAGAACACGTTCCCCAAGGGCGAGCCCGATCTGAAGAAGG

AGAGCGAGGACGGACAAGTATCCCCGTGTGCATCCGCGAGGCGGTCAGAC

AGGTGCTCAAAGGCTACGACGTGGACGCTGGTGCCCATGCCTGGTAGCGT

GTCAACTGGTCCAGAAAGAACAAGCCTGACGTCAAGCGGCCCATGAACGC

CTTCATGGTGTGGGCGCAGGCGGAGCGCACGACGCTCGCGGACCAGTACC

CGGACTTGCACAACGCCGAGCTCAGCCAGACGCTGGGCAAGCTCTGGCGA

CTACTGAACGAGAGCGACGAGCGGGCCTTCGTGAGCGCAGCGGCCGGATG

AGCGGTGGCTGGTCACCATGAAGTGACACAACCCGGGATTAAACGCTACC

AGACCGCGATAGGTAGGAACAGCTGTCTCAAAATCGTGGACACATAGGCC

GGTCACACTGATAGGACACAGTGTATGCAGAGATGGAGAAGTTTATCGCC

ACACAAGGACACATTACAACAGTAGCTGGAAACGCAGACTCAGGCCAGAA

CTACCATCCTCCCGGAATTGCACCAGGCGCTATTACCCGTGAGAACTCCC

TGGAGCCAAGCAGCGGCCCGCCCAGAACACAAACAAAGCACACGAAAGCC

AATGTACTCCATCGACGGGAAATACCAACGAACTCCACAATCAGCAGCGA

ACCACCCTAATCCCCAGACGTACT

The origin sequence for SOX9 disclosed at GenBank accession number BC007951 is as follows:

(SEQ ID NO: 17)
```
  1 ctcctcctct ccaattcgcc tcccccact tggagcgggc agctgtgaac tggccacccc
 61 gcgccttcct aagtgctcgc cgcggtagcc ggccgacgcg ccagcttccc cgggagccgc
121 ttgctccgca tccgggcagc cgaggggaga ggagcccgcg cctcgagtcc ccgagccgcc
181 gcggcttctc gcctttcccg gccaccagcc ccctgccccg ggcccgcgta tgaatctcct
241 ggacccctcc atgaagatga ccgacgagca ggagaagggc ctgtccggcg cccccagccc
301 caccatgtcc gaggactccg cgggctcgcc ctgcccgtcg ggctccggct cggacaccga
361 gaacacgcgg ccccaggaga acacgttccc caagggcgag cccgatctga agaaggagag
421 cgaggaggac aagttccccg tgtgcatccg cgaggcggtc agccaggtgc tcaaaggcta
481 cgactggacg ctggtgccca tgccggtgcg cgtcaacggc tccagcaaga acaagccgca
541 cgtcaagcgg cccatgaacg ccttcatggt gtgggcgcag gcggcgcgca ggaagctcgc
601 ggaccagtac ccgcacttgc acaacgccga gctcagcaag acgctgggca agctctggag
661 acttctgaac gagagcgaga gcggccctt cgtggaggag gcggagcggc tgcgcgtgca
721 gcacaagaag gaccacccgg attacaagta ccagccgcgc ggaggaagt cggtgaagaa
781 cgggcaggcg gaggcagagg aggccacgga gcagacgcac atctccccca cgccatctt
841 caaggcgctg caggccgact cgccacactc ctcctccggc atgagcgagg tgcactcccc
901 cggcgagcac tcgggcaat cccagggccc accgacccca ccaccaccc caaaaaccga
961 cgtgcagccg ggcaaggctg acctgaagcg agaggggcgc cccttgccag aggggggcag
```

```
-continued
1021 acagccccct atcgacttcc gcgacgtgga catcggcgag ctgagcagcg acgtcatctc 1081 caacatcgag accttcgatg tcaacgagtt tgaccagtac ctgccgccca acggccaccc 1141 gggggtgccg gccacgcacg gccaggtcac ctacacgggc agctacggca tcagcagcac 1201 cgcggccacc ccggcgagcg cgggccacgt gtggatgtcc aagcagcagg cgccgccgcc 1261 accccgcag cagcccccac aggcccgcc ggcccgcag gcgccccgc agccgcaggc 1321 ggcgccccca cagcagccgg cggcacccc gcagcagcca caggcgcaca cgctgaccac 1381 gctgagcagc gagccgggcc agtcccagcg aacgcacatc aagacggagc agctgagccc 1441 cagccactac agcgagcagc agcagcactc gccccaacag atcgcctaca gccccttcaa 1501 cctcccacac tacagcccct cctacccgcc catcacccgc tcacagtacg actacaccga 1561 ccaccagaac tccagctcct actacagcca cgcggcaggc cagggcaccg gcctctactc 1621 caccttcacc tacatgaacc ccgctcagcg ccccatgtac acccccatcg ccgacacctc 1681 tgggtccct tccatcccgc agacccacag cccccagcac tgggaacaac ccgtctacac 1741 acagctcact cgaccttgag gaggcctccc acgaagggcg aagatggccg agatgatcct 1801 aaaaataacc gaagaaagag aggaccaacc agaattccct ttggacattt gtgttttttt 1861 gttttttat tttgttttgt tttttcttct tcttcttctt ccttaaagac atttaagcta 1921 aaggcaactc gtacccaaat ttccaagaca caaacatgac ctatccaagc gcattaccca 1981 cttgtggcca atcagtggcc aggccaacct tggctaaatg gagcagcgaa atcaacgaga 2041 aactggactt tttaaaccct cttcagagca agcgtggagg atgatggaga atcgtgtgat 2101 cagtgtgcta aatctctctg cctgtttgga ctttgtaatt attttttag cagtaattaa 2161 agaaaaagt cctctgtgag gaatattctc tattttaaaa aaaaaaaaa aaaa
```

Other identifying information for the human SOX9 nucleic acid and protein are as follows: ATCC® Number: MGC-14364; I.M.A.G.E. CloneID: 4299305; GenBank Definition Line: SRY (sex determining region Y)-box 9 (campomelic dysplasia, autosomal sex-reversal); Gene Symbol: SOX9; GenBank Numbers: BF688554 & BC007951; LocusID: 6662; UniGene Cluster ID: Hs.2316; Tissue Description: normal pigmented retinal epithelium; Species: *Homo sapiens*; and Vector: pOTB7.

By accessing the GenBank accession nos. or ATCC accession nos. set forth herein, one of skill in the art can access additional GenBank or ATCC Accession Nos. listed therein to obtain additional information concerning signal sequences and mature protein sequences. The information provided under the GenBank and ATCC accession numbers, including sequences for SOX9 proteins and nucleic acids (primary amino acid sequence, coding sequences, primers, etc.) is incorporated herein in its entirety.

Nucleotides and Related Molecules

A nucleotide sequence encoding SOX9 is disclosed at GenBank accession no.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556).

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

Sequences

There are a variety of amino acid and nucleic acid sequences related to, for example, SOX9 as well as any other protein disclosed herein that are disclosed on Genbank or available as cloned deposited with the ATCC, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as the SOX9 coding sequence into the cell without degradation and include a promoter yielding expression of the gene in the cells into which it is delivered (or in melanocytes specifically). In some embodiments the vectors are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, poi, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed SOX9 or vectors expressing SOX9 for example, lipids such as liposomes, such as cationic liposomes (e.g., DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95 100 (1989); Felgner et al. Proc. Natl. Acad. Sci. USA 84:7413 7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447 451, (1991); Bagshawe, K. D., Br. J. Cancer, 60:275 281, (1989); Bagshawe, et al., Br. J. Cancer, 58:700 703, (1988); Senter, et al., Bioconjugate Chem., 4:3 9, (1993); Battelli, et al., Cancer Immunol. Immunother., 35:421 425, (1992); Pietersz and McKenzie, Immunolog. Reviews, 129: 57 80, (1992); and Roffler, et al., Biochem. Pharmacol, 42:2062 2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214 6220, (1989); and Litzinger and Huang, Biochimica et Biophysica Acta, 1104:179 187, (1992)). In general, receptors are involved in pathways of endocytosis, either constitutive or ligand induced. These receptors cluster in clathrin coated pits, enter the cell via clathrin coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor level regulation. Many receptors follow more than one intracellular pathway, depending on the cell type, receptor concentration, type of ligand, ligand valency, and ligand concentration. Molecular and cellular mechanisms of receptor mediated endocytosis has been reviewed (Brown and Greene, DNA and Cell Biology 10:6, 399 409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

These delivery methods are particularly useful for delivering Sox9 to treat blood cancers, such as leukemia, lymphoma, hematopoietic cancers.

Pharmaceutical Carriers/Delivery of Pharmaceutical Products

The compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. Intravenous (IV) and intra-tumoral administration are preferred methods for treating solid tumors e.g., melanoma, although subcutaneous delivery can also be effective for treating melanoma. Topical administration is a preferred method for treating pigmentary disorders, though IV and oral routes are expected to be effective.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Therapeutic Dosage

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

In the methods and compositions for treating cancer, effective dosages are dosages that increase SOX9 levels (or increase SOX9 expression or its phosphorylation) sufficient to cause a statistically significant inhibition in melanoma cell proliferation or to cause a statistically significant reduction in PRAME expression. In the methods and compositions for treating hypopigmentary conditions, effective dosages are dosages that increase in SOX9 levels (or increase SOX9 expression or its phosphorylation) sufficient to produce a statistically significant increase melanin production.

Guidance in selecting appropriate doses for PGD2 and PGD2 receptor agonists can be found in the literature on therapeutic uses of prostaglandins, e.g., Mutoh et al. Roles of prostanoids in colon carcinogenesis and their potential targeting for cancer chemoprevention. Curr Pharm Des. 2006; 12(19):2375-82. A typical daily dosage of PGD2 used alone might range from about 0.2 µg/kg to up to 100 mg/kg of body weight or more per day, depending on the factors mentioned above. Particularly, a dosage of 1 µg/kg to up to 5 mg/kg of body weight or more per day can be administered.

Guidance in selecting appropriate doses for RA can be found in the literature on therapeutic uses of retinoic acid, and the recommendations of the FDA for this FDA-approved drug. A typical daily dosage of RA used alone might range from about 0.2 µg/kg to up to 100 mg/kg of body weight or more per day, depending on the factors mentioned above. Particularly, a dosage range of 0.5 µg/kg to up to 2 mg/kg of body weight or a dosage range from 0.5 mg/kg to 2 mg/kg or more per day can be administered.

Guidance in selecting appropriate doses for RAR agonists is provided in scientific literature easily accessed by the skilled person. Examples or RAR agonists include RA receptor agonist all-trans retinoic acid (atRA), beta-cryptoxanthin and lutein (Matsumoto Biochem Pharmacol. 2007 Jul. 15; 74(2):256-264, incorporated herein by reference for its teaching of atRA, beta-cryptoxanthin and lutein and their dosages), 9-cis-RA, at-RA and 13-cis-RA, TTNPB (Niu et al., Di Yi Jun Yi Da Xue Xue Bao. 2005 August; 25(8):935-41, incorporated herein by reference for its teaching of 9-cis-RA, at-RA, 13-cis-RA, and TTNPB and their dosages), LGD 1069, (Ngoc et al, MOLECULAR CELLULAR BIOLOGY, July 1996, p. 3350-3360, incorporated herein by reference for its teaching of LGD 1096 and its dosage). There are numerous other examples of RAR agonists in the scientific literature that can be used in the present methods and compositions.

For example, guidance in selecting appropriate doses for SOX9 can be found in the literature and in the present Examples. For example, if the SOX9 is delivered via adenovirus or lentivirus, the dosage can range from 10 ml (of purified virus supernatant) to 1000 ml (in perfusion). Also, as disclosed herein, if the amount of SOX9 administered or the amount of upregulation of SOX9 by a SOX9 expression-enhancing compound disclosed herein is enough to produce a detectable decrease in PRAME, it is an amount effective in treating cancer. Independently, if the amount of SOX9 administered or the amount of upregulation of SOX9 by a SOX9 expression-enhancing compound disclosed herein is enough to produce a detectable reduction in cancer cell proliferation, it is an amount effective in treating cancer.

A typical daily dosage of SOX9 used alone might range from about 0.2 µg/kg to up to 100 mg/kg of body weight or more per day, depending on the factors mentioned above. Particularly, a dosage of 1 µg/kg to up to 2 mg/kg of body weight or more per day can be administered.

For example, guidance in selecting appropriate doses for DP1 can be found in the literature on therapeutic uses of DP1, e.g., A typical daily dosage of DP1 used alone might range from about 0.2 µg/kg to up to 100 mg/kg of body weight or more per day, depending on the factors mentioned above. Particularly, a dosage of 1 µg/kg to up to 2 mg/kg of body weight or more per day can be administered.

Guidance in selecting appropriate doses for TS-022, a DP1 receptor agonist, can be found in the literature on therapeutic uses of DP1 receptor agonists, e.g., Suigimoto et al. Eur J Pharmacol. 2007 Jun. 14; 564(1-3):196-203 (incorporated herein by reference for its teaching of TS-022 and its dosages) and Arai et al., Eur J. Pharmacol. 2007 556:207-214 (incorporated herein by reference for its teaching of TS-022 and its dosages) A typical daily dosage of TS-022 used alone might range from about 0.2 µg/kg to up to 100 mg/kg of body weight or more per day, depending on the factors mentioned above. Particularly, a dosage of 1 µg/kg to up to 5 mg/kg of body weight or more per day can be administered. A typical topical dosage of TS-022 can range from 0.25 nM to 250 nM with intermediate doses including 2.5 nM, 25.0 nM and all other concentrations within the larger range. A further typical topical dosage of TS-022 can range from 0.01% to 0.1% (in ethanol).

Guidance for selecting appropriate doses for PGD2 (or PGD2 receptor agonist) and RA or agonist when used together, are provided herein and in the literature where administration of each of these independently is discussed. However, because of the discovery that SOX9 inhibits RA resistance in cancers where PRAME causes resistance to RA treatment (e.g., melanoma), the doses of both can be reduced. That is, PGD2 (or PGD2 receptor agonist) increases expression of SOX9, which reduces expression of PRAME, thus allowing RA to be effective at lower doses, while at the same time, the effectiveness of RA means that less PGD2 or PGD2 receptor agonist needs to be administered. This provides advantages in terms of reduced toxicity to the subject being treated.

Following administration of a disclosed composition, such as SOX9, for treating cancer or a condition of abnormal pigmentation, the efficacy of the SOX9 can be assessed in various ways well known to the skilled practitioner. For instance, one of ordinary skill in the art will understand that a composition disclosed herein is efficacious in treating cancer or a condition of abnormal pigmentation in a subject by observing that the composition reduces tumor number or size or alters pigmentation.

Other molecules that interact with SOX9, PRAME, p21 or DP1, which do not have a specific pharmaceutical function, but which may be used for tracking changes within cellular chromosomes or for the delivery of diagnostic tools for example can be delivered in ways similar to those described for the pharmaceutical products.

Methods of Making the Compositions

The compositions disclosed herein and the compositions necessary to perform the disclosed methods can be made using any method known to those of skill in the art for that particular reagent or compound unless otherwise specifically noted.

Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

Peptide Synthesis

One method of producing the disclosed proteins, such as SOX9, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) *Synthetic Peptides: A User Guide*. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) *FEBS Lett.* 307:97-101; Clark-Lewis I et al., *J. Biol. Chem.*, 269:16075 (1994); Clark-Lewis I et al., *Biochemistry*, 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

SOX9 Inhibits Proliferation of Melanoma Cell Lines

In this study the expression and the role of SOX9 in melanoma was investigated. SOX9 strongly regulates the proliferation of melanoma cell lines. It blocks cell progression from phase G1 to S through a direct and indirect regulation of the p21 promoter. Over-expression of SOX9 prevents tumorigenicity of melanoma cells both in mice and in an ex vivo human model. Studying the relative expression of SOX9 and p21 in nearly 40 melanoma samples showed that SOX9 is down-regulated in the majority of patients but that in two patients some clones expressed high levels of SOX9 concordantly with an increased expression of p21. SOX9 also promotes the differentiation of melanoma cells and decreases expression of the melanoma antigen PRAME. Through the down-regulation of PRAME, the over-expression of SOX9 restores the sensitivity of melanoma to RA leading to a strong synergistic effect when SOX9 and RA are combined. The present results show that prostaglandin D2 is able to increase the activity of SOX9 and reproduces the synergistic effect of SOX9 when combined with RA.

SOX9 Decreases the Proliferation of Melanoma Cells

In order to study the potential action of SOX9 on melanoma cell proliferation, SOX9 was transfected into several lineages of melanoma cells and their proliferation compared to those transfected with empty cDNA vectors. One mouse melanoma cell line (B16/F10 cells) and three human melanoma cell lines (A375, Mel Juso and SK Mel28 cells) were studied. After 15 d, all cell lines transfected with SOX9 showed significant decreases in proliferation (FIG. 1).

SOX9 Induces Cell Cycle Arrest in G1 Phase

As SOX9 transfected cells showed significant decreases in proliferation, the action of SOX9 on the cell cycle was studied. B16 and A375 cells were transduced with GFP or SOX9 lentivirus and were then selected with blasticidin for one week. The cells were then stained with propidium iodide and their cycle was studied with FACS analysis. Both B16 and A375 cells transduced with SOX9 showed marked increases in phase G1 of the cell cycle as compared to the GFP controls.

The Action of SOX9 on Proliferation is Mediated Through a Direct and an Indirect Action on p21

In chondrocytes, where SOX9 is known to play a key role especially during embryogenesis, SOX9 has been shown to increase p21 expression without however explaining the mechanism of action of SOX9 on p21 (9). As p21 plays a major role in cell cycle regulation, the action of SOX9 on p21 was investigated in A375 and in Mel Juso melanoma cells. Those cells were transduced with SOX9 lentivirus or GFP lentivirus as a control. One week after selection with blasticidin, proteins were extracted and were analyzed using immunoblotting with p21, SOX9, MITF and β-catenin antibodies. p21 expression was strongly increased concordantly with the increased expression of SOX9. At the same time, MITF expression was also analyzed. The expression level of MITF was very low in control conditions in both cell lines and was increased after transfection of SOX9 (especially in A375 cells). Those data are concordant with the results in normal human melanocytes where SOX9 was demonstrated to bind the MITF promoter and to increase its expression (Example 2). The β-catenin pathway is up-regulated in one third of melanomas but mutations of β-catenin appear to be rare (10). The putative action of SOX9 on the expression of β-catenin was investigated. Interestingly, after over-expression of SOX9, the expression of β-catenin was decreased.

To confirm these findings, SOX9 cDNA was transfected into A375 cells. After 48 h, the cells were fixed and analyzed using immunofluorescence with the antibodies of interest. Again, in cells transfected with SOX9, p21 and MITF were up-regulated whereas β-catenin expression was decreased. Importantly, the nuclear localization of β-catenin was the most strongly reduced when SOX9 was over-expressed. The experiment was also reproduced in Mel Juso cells with the same results.

MITF has been recently shown to regulate the cell cycle of melanoma cells through a direct action on the p21 promoter (1). Based on the fact that SOX9 activates the MITF promoter (Example 2), as confirmed for MITF in melanoma cell lines (see above), it is suspected that the action of SOX9 on p21 works through this up-regulation of MITF. However, analysis of the p21 promoter showed several potential binding sites for SOX9. The potential binding of SOX9 on the p21 promoter in A375 cells was further analyzed using chromatin immunoprecipitation (CHIP) assay. Indeed, incubation with SOX9 antibody showed a positive binding with the p21 promoter whereas none was found with HSP70 used as a control. Thus, SOX9 is able to increase p21 expression when acting indirectly through an increase of MITF but also directly by binding and activating the p21 promoter, explaining the strong increase of p21 detected after the over-expression of SOX9 and its powerful action on proliferation.

The proliferation assay in A375 cells was reproduced comparing the over-expression of SOX9 and the over-expression of SOX9 following by silencing of p21 to control levels. After 10 d, the decrease of proliferation of SOX9 transfected cells was found but the silencing of p21 allowed cells to better recover their proliferation. There was a clear differentiation observed in SOX9 transfected cells with melanosomes accumulating at the end of the dendrites.

Figure 2B:
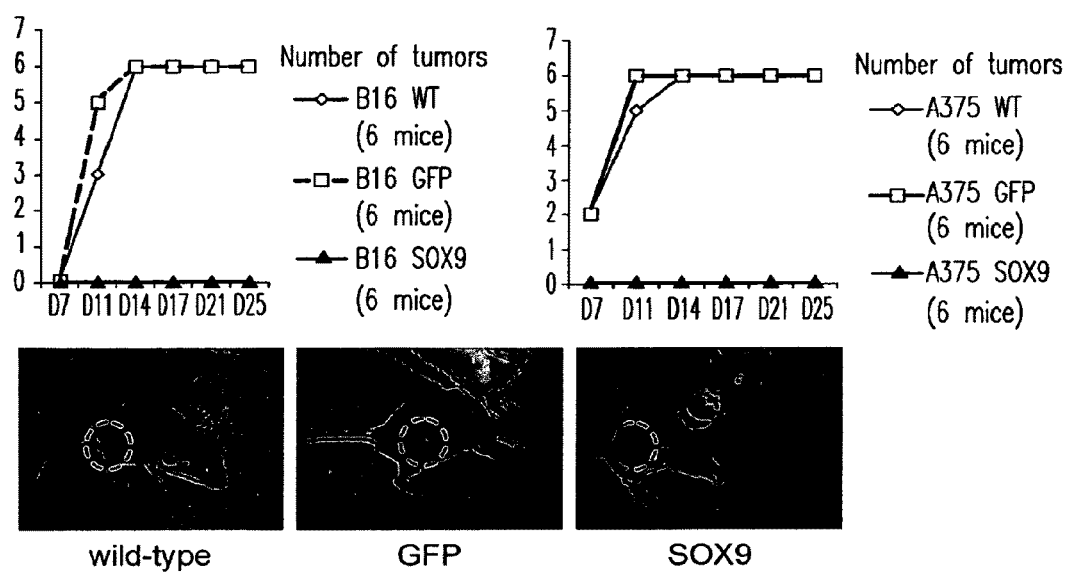

The Over-Expression of SOX9 Prevents Proliferation of Melanoma Cells in Human Reconstructed Skin Model and in Mice The strong inhibition of proliferation observed in melanoma cells in vitro following SOX9 over-expression lead to testing of the tumorigenicity of those transfected cells in vivo. A melanoma reconstructed model was used. A375 melanoma cells were transduced with GFP or SOX9 lentivirus and then were selected with blasticidin for a week. Next, $3 \times 10^5$ A375 cells were put on reconstructed skin. After 10 d, A375 wild type and A375 GFP cells had formed numerous tumors within the epidermis with some rare cells invading the dermis. In contrast, A375 cells over-expressing SOX9 did not proliferate and did not form any tumors. At d 17, the difference was even more obvious with large tumors and invasion of the dermis by A375 wild type and GFP cells whereas most of A375 SOX9 cells went into apoptosis and the remaining ones did not grow (FIGS. 2A and 2B). In a further test, A375 and B16 cells were transduced with GFP or SOX9 lentivirus and after 1 week of selection, $1 \times 10^6$ of those A375 and B16 cells were injected subcutaneously in nude or C57Bl6 mice, respectively. Both wild type and GFP cells induced tumors in the mice whereas SOX9 transduced cells did not induce any tumors (FIG. 2C1).

Comparative Expression of SOX9 in Normal Skin and in Melanomas

SOX9 is expressed in melanocytes in vivo and its expression is up-regulated after UVB exposure (see Example 2). Using immunohistochemistry on melanoma tissue array from 39 patients with pigmented or non pigmented melanomas, the relative expression of SOX9 and p21 among these patients was studied and compared to normal skin samples exposed or non-exposed to UVB. In agreement with the results in Example 2, SOX9 is expressed in normal human melanocytes. This expression was increased after UVB exposure. However, p21 staining was negative in unexposed skin whereas a weak staining was observed after UVB exposure. To localize melanocytes within the skin, co-staining with SOX9 and MART1 (as a melanocytic marker) was performed and this confirmed that SOX9 is expressed by melanocytes. Interestingly, 37 of the 39 melanoma samples showed a negative staining for SOX9 and p21 but in two samples some melanoma cells highly expressed SOX9. In these two melanomas, most cells with high expression of SOX9 also showed high expression of p21 emphasizing the strong relationship between SOX9 and p21 in melanoma cells.

Figure 3A:
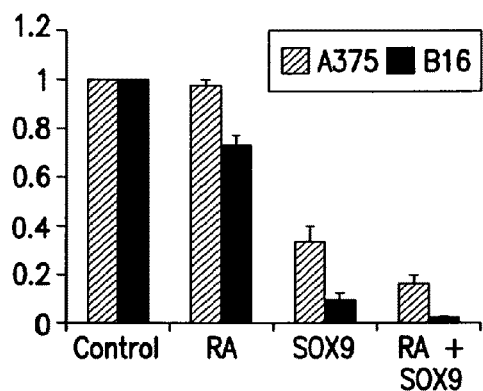
FIG. 3. Prostaglandin D2 restores retinoic acid (RA) sensitivity by increasing SOX9 expression that in turn down-regulates PRAME. (A) Proliferation assay of A375 and B16 cells, which are resistant and sensitive to RA, respectively. Addition of RA $10^{-7}$ M has no effect on A375 cells and decreases the proliferation of B16 cells. Transfection of SOX9 induces a strong decrease in proliferation in both cell lines. Addition of RA $10^{-7}$M to SOX9 transfected cells shows a synergistic decrease in proliferation, including A375 cells in which sensitivity to RA is restored. (B) Immunoblotting of A375 cells treated for 72 h with prostaglandin D2 (PGD2) 0.5 µg/µl and compared to untreated cells (Basal). (C) Proliferation assay of A375 cells treated with RA $10^{-7}$ M, PGD2 0.5 µg/µl, and combination of both as compared to untreated controls. Upper panels show macroscopic view of the proliferative clones and lower panels the same clones at a magnification of 10×. (D) Graphic representation of the proliferation assay with RA and PGD2 in A375 and B16 cells.
Figure 5:
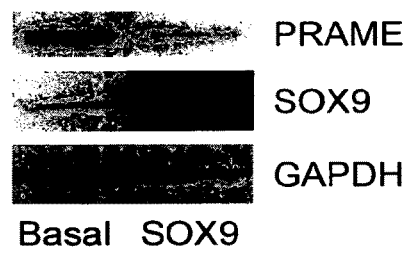
FIG. 5. SOX9 down-regulates PRAME. A375 melanoma cells were transduced with SOX9 lentivirus or GFP lentivirus as a control. One week after transduction and selection with blasticidin, proteins were extracted and were analyzed by immunoblotting using PRAME, SOX9 and GAPDH antibodies.

SOX9 Decreases PRAME Expression in Melanoma Cells and Restores Retinoic Acid Sensitivity PRAME is a melanoma antigen that has been recently shown to be a dominant repressor of the retinoic acid (RA) receptor and its silencing restores the sensitivity to RA (11, 12). SOX9 promotes differentiation, at least in normal melanocytes, thus whether SOX9 could have an action on the expression of PRAME in melanoma cells was determined. A375 and Mel Juso cells are both known to express high levels of PRAME and to be resistant to RA. Those cells were transduced with SOX9 lentivirus or GFP lentivirus as a control. One week after selection with blasticidin, proteins were extracted and were analyzed using immunoblotting (FIG. 5). Interestingly, PRAME expression was decreased after over-expression of SOX9 in both types of cells. To check if this decrease was physiologically relevant, an additional proliferation assay on A375 cells transfected or not with SOX9 and with or without additional treatment with RA was performed. As expected, RA showed no effect on A375 control but interestingly it enhanced the effect of the SOX9 transfection inducing an even stronger decrease in proliferation (FIG. 3A).

In B16 cells, RA by itself induced a decrease in proliferation but also enhanced the effect of the transfection with SOX9.

Figure 3B:
Figure 3C:
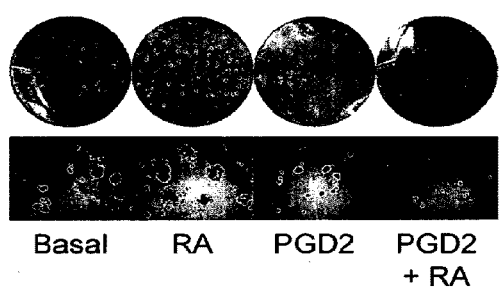
Figure 3D:
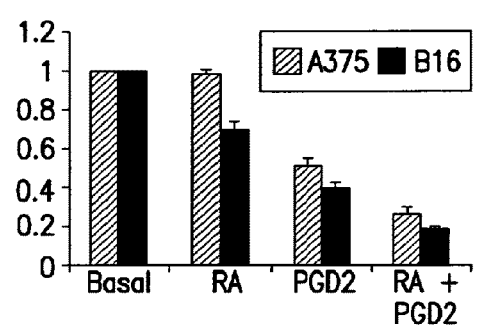
Figure 4:
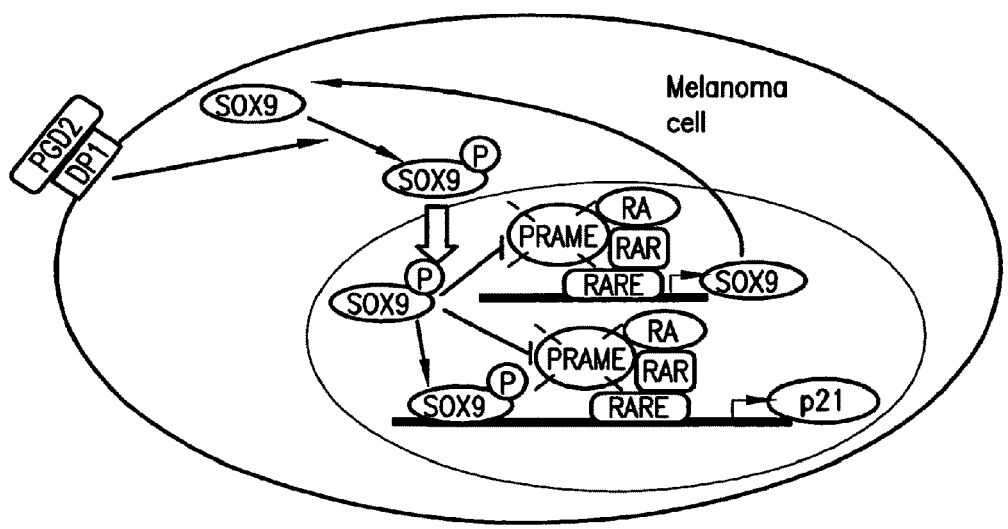
FIG. 4. Synergistic combination of PGD2 and RA in melanoma cells. PGD2 induces an increase of SOX9 and promotes its nuclear translocation through its phosphorylation. SOX9 activates the p21 promoter and down-regulates PRAME. RA is no longer inactivated due to PRAME and activates both the p21 and the SOX9 promoters leading to a powerful synergistic effect on proliferation.

Up-Regulation of SOX9 by Prostaglandin D2 and Synergistic Action of SOX9 with Retinoic Acid—Combination Treatment for Melanoma SOX9 shows strong inhibition of melanoma proliferation in vitro and in vivo and thus appears as a target of choice for gene therapy. SOX9 has been extensively studied in chondrocytes due to its key role for collagen II synthesis. In those cells, prostaglandin D2 (PGD2) has been shown to increase SOX9 activity by promoting its phosphorylation and its nuclear translocation (13). Interestingly, PGD2, and more recently its metabolite Δ2-PGJ2, have been shown to decrease the proliferation of melanoma cells and other cancer cells although their mechanism of action was not fully elucidated (14-17). First, S35 labeling was performed on A375 cells treated or not treated with PGD2 for 72 h. Proteins were then extracted and immunoprecipitated with SOX9 and PRAME antibodies (GAPDH was used as a control). SOX9 was increased after treatment with PGD2 whereas PRAME was decreased (FIG. 3B). The over-expression of SOX9, through the decrease of PRAME, was able to restore RA sensitivity and had a synergistic effect on melanoma proliferation. A further proliferation assay with or without RA treatment, using PGD2 instead of the transfection with SOX9, was performed. PGD2 inhibited A375 proliferation, whereas RA showed no effect. But interestingly, as observed with the over-expression of SOX9, the proliferation assay showed a clear synergistic effect when PGD2 and RA were combined (FIGS. 3C and 3D). The experiment was reproduced in B16 cells which are sensitive to RA and also revealed a synergistic effect of the two treatments (FIG. 3D).

These new findings bring new insights for the understanding of proliferation and differentiation pathways in melanoma and provide a novel approach for a combination therapy.

Materials and Methods

Cell Culture and Reagents.

B16/F10 melanoma cells, SKMel 28 and A375 cells were obtained from the ATCC (Manassas, Va., USA). Mel Juso cells are a generous gift from Dr. Hornyak at the National Cancer Institute. A375, SK Mel 28 and B16 cells were grown at 37° C. under 5% $CO_2$ in DMEM supplemented with 7% Fetal Bovine Serum (FBS) and penicillin (100 U/ml) and streptomycin (50 ug/ml). Mel Juso cells were grown at 37° C. under 5% $CO_2$ in RPMI medium supplemented with 10% FBS and penicillin (100 U/ml) and streptomycin (50 ug/ml). Retinoic acid ($10^{-7}$M) and Prostaglandin D2 (0.5 ug/ml) were purchased from Sigma-Aldrich (St-Louis, Mo., USA).

Reconstructed Skin.

The melanoma skin Model® was obtained from MatTek Corp., Ashland, Mass., USA. Normal human keratinocytes and fibroblasts were obtained from Caucasian neonatal foreskin tissues. A375 cells (wild type, or transduced with GFP or SOX9 lentivirus) were added to the skin construct. The melanoma skin Models® were grown via air/liquid interface locating the maintenance MCDB 153 Basal Medium (MatTek Cor., Ashland, Mass., USA) underneath. The culture medium was renewed every two days.

Plasmid and Lentivirus Construction, siRNA and Transfection.

The SOX9 cDNA was purchased from the ATCC (ATCC Deposit No.: MGC-14364; the sequence of this clone is incorporated herein by this reference) and after amplification was ligated into the pcDNA3.1 vector (Invitrogen) using the manufacturer's protocol. The constructs were confirmed by sequence analysis. As a negative control, the pcDNA3.1 vector with no insertion was used. Transfection was performed for melanocytes using lipofection with lipofectamine 2000 (Invitrogen). Cells were seeded one day in advance and were transfected according to the manufacturer's instructions. The on-target plus SMARTpool® (Dharmacon, Lafayette, Colo., USA) SiRNA for human p21 was used to silence p21 expression. A commercial negative control sequence (Invitogen) was used to monitor for off-target effects. Transfections for silencing experiments were performed using RNAiMAX (Invitrogen). The amount of DNA used for each transfection was 2 μg per $1 \times 10^6$ cells whereas SiRNA was used at 100 nM. The SOX9 and GFP lentivirus were generated by cloning the SOX9 or GFP cDNA into the pLenti 6.2 (Invitrogen).

Immunoblotting.

Cells were solubilized in M-PER® mammalian protein extraction reagent (Pierce Biotechnology, Rockford, Ill., USA) containing Protease Inhibitor cocktail (Roche, Mannheim, Germany). Protein concentrations of extracts were measured using the BCA protein assay kit (Pierce, Rockford, Ill., USA). Cell extracts (30 μg) were separated on SDS polyacrylamide gels (Invitrogen). After electrophoresis, proteins were transferred electrophoretically from the gels to Invitrolon PVDF transfer membranes (Invitrogen). The filters were incubated with antibodies to SOX9 (rabbit 1 μg/ml; Chemicon, Temecula, Calif., USA), PRAME (rabbit 1 μg/ml; Abcam, Cambridge, UK), p21 (mouse 1:2000, Cell Signaling, Danvers, Mass., USA), MITF (mouse 1:8000, generous gift from Dr. Heinz Arnheiter at NIMH), β-catenin (mouse, 1; 500, Santa Cruz) or GAPDH (rabbit 1:10,000, Santa Cruz) for 1 h at 23° C. to overnight at 4° C. (depending on the antibody) and were then incubated with horseradish peroxidase-linked anti-rabbit, anti-mouse or anti-goat whole antibodies (at 1:1, 0000, GE Healthcare, Buckinghamshire, UK) at room temperature for 1 h. Antigens were detected using ECL-plus Western Blotting Detection System (GE Healthcare). Each experiment was performed at least in triplicate.

Immunocytochemical Staining.

Melanocyte cultures in two well Lab-Tek chamber slides (Nalge Nune International Corp., Naperville, Ill., USA) were processed for indirect fluorescence to detect the expression of proteins using primary antibodies to SOX9 (rabbit 1:50, Abcam), MITF (mouse 1:500, generous gift from Dr. Heinz Arnheiter), p21 (mouse 1:50, DAKO, Glostrup, Denmark) and β-catenin (mouse, 1; 50, Santa Cruz). Bound antibodies were visualized with appropriate secondary antibodies, Alexa Fluor® 488 goat anti-rabbit IgG (H+L) (Molecular Probes, Inc., Eugene, Oreg., USA), Alexa Fluor® 594 mouse anti-rabbit IgG (H+L) (Molecular Probes), Alexa Fluor® 488 goat anti-mouse IgG (H+L) (Molecular Probes) or Alexa Fluor® 594 goat anti-mouse IgG (H+L) (Molecular Probes) at 37° C. for 30 min at 1:500 dilution with 5% goat serum. DAPI (Vector, Burlingame, Calif.; USA) was used as a counterstain. The green fluorescence produced by Alexa 488®, red produced by Alexa 594®, and blue by DAPI was observed and captured using a Leica DMR B/D MLD fluorescence microscope (Leica, Wetzlar, Germany) and a Dage-MTI 3CCD 3-chip color video camera (Dage-MTI, Michigan City, Ind., USA).

Immunohistochemistry.

Melanoma tissue arrays were obtained from BioChain Institute Inc (Hayward, Calif., USA) (lot No: A902061). Skin specimens obtained from the back were taken from healthy volunteers after informed consent. The expression of proteins of interest was detected by indirect immunofluorescence using the following as primary antibodies: SOX9 (rabbit 1:50, Abcam), p21 (mouse 1/50; DAKO), S100 (rabbit 1/100; Abcam) and MART1 Ab-3 (mouse 1:100; NeoMarkers).

Bound antibodies were visualized with appropriate secondary antibodies and fluorescence was observed and analyzed using a fluorescence microscope as detailed above.

Proliferation Assay.

The cells were transfected with a pBabe vector to give them a resistance to puromycin. At the same time, they were transfected with SOX9 cDNA or empty vector as control. Depending on the experiment, cells were also transfected the day after with SiRNA p21 or SiRNA Mock. After 10 to 15 d, the clones were fixed and stained with crystal violet. Proliferation was measured according to the optical density of the color.

FACS Analysis.

Cells were harvested and incubated at 4° C. for 1 h with a solution containing 0.1% Triton X100, 0.1% Na Citrate and 50 µg/ml propidium iodide. Cell cycle was then analyzed using Cell QuestPro software (BD, Franklin Lakes, N.J., USA).

Chromatin Immunoprecipitation.

ChIP assays were performed (as Invitrogen's protocol) using 4 µg of SOX9 antibody (Chemicon, Billerica, USA) or 4 µg of non-specific IgG (Invitrogen). The DNA recovered was subjected to amplification by PCR before analysis using agarose gel electrophoresis. The primers used for the PCRs were the human MITF promoter region (5'-GATGAT-GTCTCCTCCAAAGG-3' (SEQ ID NO:11) and 5'-AGC-CCTACGAGTTTGGTCTT-3' (SEQ ID NO:12)) and the GAPDH promoter (5'-CGGTGCGTGCCCAGTTG-3' (SEQ ID NO:13) and 5'-GCGACGCAAAAGAAGATG-3' (SEQ ID NO:14). Melanin Content Assay. Melanin content was determined as described previously (60). Melanin contents are expressed as ng of melanin divided by the total protein in µg. Values are reported compared to values obtained in controls and are reported as ratios. Each experiment was repeated at least 3 times. Statistical Analysis. Data are presented as means.±.SD. Student's t test was used to analyze differences. Values of $p<0.05$ are considered significant.

Animal Model.

One week after transduction and selection, $1\times10^6$ B16 mouse melanoma cells (wild type, GDP transduced or SOX9 transduced) were injected subcutaneously into C57B16 mice while $1\times10^6$ A375 human melanoma cells (wild type, GDP transduced or SOX9 transduced) were injected into nude mice. Mice were then monitored for date of tumor appearance and their size until d 25 or if the tumor became 2 cm in diameter. Both experiments were done in 18 mice in duplicate in two separate time.

Statistical Analysis.

Data are presented as means±SD. Student's t test was used to analyze differences. Values of $p<0.05$ are considered significant.

Example 2

SOX9 is Expressed in Melanocytes and has a Role in UVB-Induced Melanocyte Differentiation and Pigmentation SOX9 is expressed in vitro and in vivo in normal melanocytes and regulates UVB induced pigmentation through a direct activation of the MITF promoter. SOX9 directly regulates MITF, one of the master genes for melanogenesis, which has also been demonstrated to regulate melanocyte and melanoma cell proliferation.

Materials and Methods

Reagents, Cell Lines, and Culture Conditions.

Neonatal and adult human foreskin melanocytes (a-LP, n-LP, n-MP and n-DP) were obtained from Cascade Biologics, Inc (Portland, Oreg., USA). B16/F10 melanoma cells and HeLa cells were obtained from the ATCC (Manassas, Va., USA). Cultured melanocytes were grown in melanocyte growth medium consisting of Medium 254 and HMGS (both from Cascade Biologics, Inc). Melanocytes from the third to ninth passage were used in these experiments. B16 cells were grown at 37° C. under 5% $CO_2$ in DMEM supplemented with 7% fetal bovine serum (FBS) and penicillin (100 U/ml) and streptomycin (50 µg/ml). HeLa cells were grown at 37° C. under 5% $CO_2$ in DMEM supplemented with 10% FBS and penicillin (100 U/ml) and streptomycin (50 µg/ml). Forskolin (20 µM), αMSH (100 nM) and H89 (5 µM) were purchased from Sigma-Aldrich (St-Louis, Mo., USA). Recombinant ASP was purified from fresh culture supernatants of insect cell culture infected with a baculovirus construct that contained the mouse cDNA (Eukaryotic Expression Group, NCI, Frederick, Md., USA). The purification protocol is based on ion-exchange chromatography and size-exclusion chromatography (Protein Purification Group, NCI, Frederick, Md., USA).

Reconstructed Skin.

The epidermal equivalent MelanoDerm® was obtained from MatTek Corp. (Ashland, Mass., USA), normal human keratinocytes and melanocytes used were obtained from Asian neonatal foreskin tissues. MelanoDerms were grown at the air/liquid interface of the maintenance medium MEL-NHM-113 (MatTek Corp) and culture medium was renewed every 2 d.

Plasmid Construction, siRNA and Transfection.

The SOX9 cDNA was purchased from the ATCC and after amplification was ligated into the pcDNA3.1 vector (Invitrogen). The constructs were confirmed by sequence analysis. As a negative control, the pcDNA3.1 vector with no insertion was used. Transfection was performed for melanocytes using lipofection with lipofectamine 2000 (Invitrogen). Cells were seeded 1 day in advance and were transfected according to the manufacturer's instructions. For the study of the effects of SOX9 over-expression on SOX10, DCT and tyrosinase protein expression and production of melanin, the transfection was done using the Amaxa system (Gaithersburg, Md., USA) according to the manufacturer's instructions. The on-target plus SMARTpool® (Dharmacon, Lafayette, Colo., USA) SiRNA for human SOX9 was used to silence SOX9 expression. A commercial negative control sequence (Invitrogen) was used to monitor for nonspecific effects.

Transfections for silencing experiments were performed using oligofectamine (Invitrogen). The amount of DNA used for each transfection was 2 µg per $1\times10^6$ cells whereas SiRNA was used at 100 nM. After 24 to 48 h, depending experimental protocol, the transfected cells were harvested for various analyses including western blotting.

RT-PCR.

Total RNA was reverse-transcribed using SuperScript III (Invitrogen). PCR reactions consisted of 25 cycles for β-actin and 35 cycles for SOX9 using Taq DNA polymerase (Invitrogen). PCR products for β-actin and SOX9 were 838 bp, and 288 bp, respectively, and were electrophoresed in parallel with DNA molecular mass markers (Invitrogen). Total RNA was reverse-transcribed using SuperScript III (Invitrogen). PCR reactions consisted of 25 cycles for β-actin and 35 cycles for SOX9 using Taq DNA polymerase (Invitrogen). PCR products for β-actin and SOX9 were 838 bp, and 288 bp, respectively, and were electrophoresed in parallel with DNA molecular mass markers (Invitrogen). Oligonucleotide primers used for PCR were based on mRNA sequences as follows: human SOX9 sense primer 5'-GGGAAGGCCGC-CCAGGGCGA-3' (SEQ ID NO:5); human SOX9 antisense primer 5'-TGCCTTGCCCGACTGCAGTTCT-3' (SEQ ID NO:6), β-actin sense primer 5'-ATCTGGCACCACACCT-TCTACAATGAGCTGCG-3' (SEQ ID NO:7); β-actin antisense primer 5'-CGTCATACTCCTGCTTGCTGATCCA-CATCTGC-3' (SEQ ID NO:8). Each experiment was repeated at least in triplicate independently.

Immunoblotting.

Cultures in 100 mm dishes were solubilized in 500 μM-PER® mammalian protein extraction reagent (Pierce Biotechnology, Rockford, Ill., USA) and Protease Inhibitor cocktail (Roche, Mannheim, Germany). Protein concentrations of extracts were measured using the BCA protein assay kit (Pierce, Rockford, Ill., USA). Cell extracts (20 μg) were separated on 8-16% gradient SDS polyacrylamide gels (Invitrogen). After electrophoresis, proteins were transferred electrophoretically from the gels to Invitrolon PVDF transfer membranes (Invitrogen). The filters were incubated with antibodies to SOX9 (rabbit 1:500; Abcam, Cambridge, UK), SOX10 (goat 1:200; Santa Cruz, Santa Cruz, Calif., USA), DCT (1:2,000; (22)), Tyrosinase (rabbit 1:10,000; (22)), or GAPDH (rabbit 1:10,000, Santa Cruz) for 1 h at 23° C. to overnight at 4° C. (depending on the antibody) and were then incubated with horseradish peroxidase-linked anti-rabbit, anti-mouse or anti-goat whole antibodies (at 1:1,0000, GE Healthcare, Buckinghamshire, UK) at room temperature for 1 h. Antigens were detected using ECL-plus Western Blotting Detection System (GE Healthcare). Blots were quantitated using Scion Image Software (Scion Corp., Frederick, Md., USA). Each experiment was performed at least in triplicate.

Immunocytochemical Staining.

Melanocyte cultures in two well Lab-Tek chamber slides (Nalge Nune International Corp., Naperville, Ill., USA) were processed for indirect fluorescence to detect the expression of proteins using primary antibodies to SOX9 (rabbit 1:50, Abcam), MITF-ab3 (mouse 1:100 dilution; NeoMarkers, Fremont, Calif., USA), DCT (rabbit 1:7,500; (22)) and Tyrosinase (rabbit 1:700; (22)). Bound antibodies were visualized with appropriate secondary antibodies, Alexa Fluor® 488 goat anti-rabbit IgG (H+L) (Molecular Probes, Inc., Eugene, Oreg., USA), Alexa Fluor® 594 mouse anti-rabbit IgG (H+L) (Molecular Probes), Alexa Fluor® 488 goat anti-mouse IgG (H+L) (Molecular Probes) or Alexa Fluor® 594 goat anti-mouse IgG (H+L) (Molecular Probes) at 37° C. for 30 min at 1:500 dilution with 5% goat serum. DAPI (Vector, Burlingame, Calif.; USA) was used as a counter-stain. The green fluorescence produced by Alexa 488®, red produced by Alexa 594®, and blue by DAPI was observed and captured using a Leica DMR B/D MLD fluorescence microscope (Leica, Wetzlar, Germany) and a Dage-MTI 3CCD 3-chip color video camera (Dage-MTI, Michigan City, Ind., USA).

Immunohistochemistry.

Skin specimens obtained from the dorsal areas were taken from healthy volunteers after informed consent. The expression of proteins of interest was detected by indirect immunofluorescence using the following as primary antibodies: SOX9 (rabbit 1:50, Abcam) and MART1 Ab-3 (mouse 1:100 dilution; NeoMarkers). Bound antibodies were visualized with appropriate secondary antibodies and fluorescence was observed and analyzed using a fluorescence microscope as detailed above.

Tissue In Situ Hybridization.

Oligonucleotide probes specific for human SOX9 were designed. Target sites were selected based on the analysis of sequence matches and mismatches BLAST (GenBank). Probes showed no evidence of cross-reaction with sequences of other genes including other SOX family genes. Oligonucleotide probes specific for human SOX9 were designed. Target sites were selected based on the analysis of sequence matches and mismatches BLAST (GenBank). Probes showed no evidence of cross-reaction with sequences of other genes including other SOX family genes. Best results were obtained with the following probes: sense primer 5'-CATACGATT-TAGGTGACACTATAG-gggcaggcggaggcagagga-3' (SEQ ID NO:9); antisense primer 5'-GCGCGTAATACGACT-CACTATAGGG-gctgctcagctcgccgatgtcc-3' (SEQ ID NO:10). The probes were 3' tailed with digoxigenin-11-dUTP with a DIG RNA labeling kit (Roche, Basel, Switzerland), according to recommendations of the manufacturer. TISH was carried out as described previously with minor modifications (61). Briefly, after deparaffinization and rehydration, skin sections were immersed in antigen retrieval solution and heated in a microwave for 12 min then cooled for 20 min. Slides were then washed in glycine solution (2 mg/ml in PBS) for 10 min then washed twice in PBS, and placed in 200 ml acetylation buffer (0.1 M triethylamine, pH 8.0, containing 0.25% acetic anhydride) for 15 min. After washing in 4×SSC for 10 min, samples were incubated in prehybridization solution (2×SSC, 50% deionized formamide) for 1 h at 47° C. After overnight hybridization at 47° C., samples were placed in hybridization solution (62) containing 10 μl purified DIG-labeled antisense riboprobe. Samples were then incubated in 10 mM Tris-HCl, 0.5 M NaCl and 0.25 mM EDTA (TNE) buffer, treated with RNaseA for 30 min, and returned to TNE buffer for 3 min, all at 37° C. After washing in 0.1×SSC for 15 min at 47° C., samples were blocked for 30 min and incubated with anti-DIG/HRP conjugate (DAKO, Carpinteria, Calif., USA) for 40 min at room temperature. For detection, the tyramide signal amplification system (GenePoint kit, DAKO) and VIP solution (Vector) were used according to the manufacturer's instructions. Samples were observed and photographed in a Leica DMRB microscope. For double staining protocols to detect melanocytes, the experiment was stopped before fixation and a standard immunohistochemistry was done as described above, starting with the primary antibody incubation.

Metabolic Labeling.

Radioactive metabolic labeling and immunoprecipitation was performed as described previously (58). Where indicated, cells were irradiated with 21 mJ/cm$^2$ UVB and/or chemical agents were added from the "pulse" period to the "chase" period. Cell extracts were incubated with normal rabbit serum (Vector, Burlingame, Calif., USA) and were then incubated with protein G beads (GE Healthcare). The supernatants were incubated with SOX9 (Abcam) or GAPDH (Santa-Cruz) antibodies. The immune-complexes were separated by incubation with beads and were further washed with immunoprecipitate lysis buffer. The pellets were eluted, electrophoresed and visualized by autoradiography.

Luciferase Assay.

B16 melanoma cells or HeLa cells were seeded in 24-well dishes and were transfected with 0.3 μg of the luciferase reporter plasmid and 0.05 μg of pCMVβGal (Promega, Madison, Wis., USA) to control the variability of transfection efficiency. In some experiments, SOX9 was over-expressed using 0.1 μg of the pcDNA3 encoding SOX9, or was silenced with SOX9 siRNA (100 nM). Empty pcDNA3 or siRNA scrambles were used as controls depending on the experiments. All transfections were made with Lipofectamine (Invitrogen) according to the instructions of the manufacturer. Thirty-six h later, cells were washed with a saline phosphate buffer and lysed with reporter lysis buffer (Promega). Soluble extracts were harvested and assayed for luciferase and β-galactosidase activities. All transfections were repeated at least 3 times using different plasmid preparations and gave similar results. The pMITF wild-type and mutants, pDCT, pTYR, and pCRE constructs used were described previously (26, 43, 59).

Chromatin Immunoprecipitation.

ChIP assays were performed (as Invitrogen's protocol) using 4 μg of SOX9 antibody (Chemicon, Billerica, USA) or 4 μg of non-specific IgG (Invitrogen). The DNA recovered was subjected to amplification by PCR before analysis using agarose gel electrophoresis. The primers used for the PCRs were the human p21 promoter region (5'-TGATGTGCCA-CAGTTCACAA-3' (SEQ ID NO:1) and 5'-TCCTGC-CAGTTTTCCTGTTC-3' (SEQ ID NO:2) and the HSP70 promoter (5'-CCTCCAGTGAATCCCAGAAGACTCT-3' (SEQ ID NO:3) and 5'-TGGGACAACGGGAGT-CACTCTC-3' SEQ ID NO:4). Animal model. One week after transduction and selection, 1.times.10.sup.6 B16 mouse melanoma cells (wild type, GDP transduced or SOX9 transduced) were injected subcutaneously into C57Bl6 mice while 1.times.10.sup.6 A375 human melanoma cells (wild type, GDP transduced or SOX9 transduced) were injected into nude mice. Mice were then monitored for date of tumor appearance and their size until d 25 or if the tumor became 2 cm in diameter. Both experiments were done in 18 mice in duplicate in two separate time. Statistical analysis. Data are presented as means.±.SD. Student's t test was used to analyze differences. Values of p<0.05 are considered significant.

Melanin Content Assay.

Melanin content was determined as described previously (60). Melanin contents are expressed as ng of melanin divided by the total protein in μg. Values are reported compared to values obtained in controls and are reported as ratios. Each experiment was repeated at least 3 times.

Statistical Analysis.

Data are presented as means±SD. Student's t test was used to analyze differences. Values of p<0.05 are considered significant.

Results

SOX9 is Expressed in Melanocytes In Vivo

To determine whether SOX9 mRNA is expressed in human skin a specific probe directed against SOX9 was designed and a TISH study performed. A strong positive staining in the epidermis was detected with the anti-sense probe whereas staining with the sense probe was negative, showing the presence of SOX9 RNA in the skin. To differentiate melanocytes from keratinocytes, The TISH protocol was coupled with standard immunohistochemistry performed with antibodies directed against MART1, a specific marker of melanocytes. Melanocytes identified by MART1 were also stained by the SOX9 TISH probe demonstrating that melanocytes express SOX9 in human skin in vivo. The presence of SOX9-positive melanocytes was also detected at the protein level with immunohistochemistry using antibodies directed against SOX9 and MART1.

SOX9 is Up-Regulated by UVB Exposure

To investigate whether SOX9 is regulated during melanocyte differentiation, melanocytes were exposed to their most common external stimulus, UV radiation. NHM obtained from adult lightly pigmented skin (a-LP) were irradiated in culture with 21 mJ/cm$^2$ UVB and compared to non-irradiated controls. RT-PCR showed that the expression level of SOX9 was increased 1 h after UVB exposure compared to non-irradiated cells. At the protein level, an increase in SOX9 was observed starting 2 h after the UVB exposure, increased further until 8 h and then decreased at 24 h. The stimulation of SOX9 expression was confirmed by immunoprecipitation of $^{35}$S-labeled SOX9. Finally, the basal expression of SOX9 in n-LP and in n-DP NHM were compared using immunoblotting. The darker melanocytes expressed more SOX9 than did the lightly pigmented melanocytes.

The Action of UVB on SOX9 is Mediated by cAMP and PKA

As the cAMP pathway plays a key role in regulating pigmentation and mediates most of the effects of UV on melanogenesis (36), the effect of cAMP on SOX9 was investigated. After $^{35}$S metabolic labelling, NHM were exposed to 21 mJ/cm$^2$ UVB or to forskolin, a cAMP stimulating agent, and then SOX9 was immunoprecipitated. Treatment with either UVB or forskolin led to increased expression of SOX9. PKA, the most important downstream target of cAMP, can be inhibited by H89. The expression of SOX9 and SOX9 phosphorylated at serine 181 were both increased after UVB exposure and in both cases, pretreatment with H89 prevented the increased expression of SOX9 by UVB.

The up-regulation of SOX9 after forskolin treatment was also observed in NHM using immunocytochemistry. Four hr after forskolin treatment, the cells were fixed and stained with SOX9 antibodies. An increased expression of SOX9 was noted in NHM treated with forskolin. A reconstructed skin model (Melanoderm®) was used to assess the effect of UVB on SOX9 expression in the skin. After 4 d of growth, Melanoderms were exposed or not to 21 mJ/cm$^2$ UVB. The samples were fixed 8 hr after the UV irradiation, and were then double stained with SOX9 and MART1 antibodies to identify melanocytes. The results confirmed the increased SOX9 staining in melanocytes with a predominant nuclear localization after UVB exposure.

SOX9 is Down-Regulated by ASP

ASP is an antagonist of the melanocortin I receptor (MC1R) which plays a key role in regulating pigmentation (37). ASP inhibits melanin formation in mouse melanocytes and in melanoma cells as well as in NHM (38-40). NHM obtained from neonatal moderately pigmented skin (n-MP) were treated with ASP. RNAs were then extracted, and RT-PCR showed that the expression level of SOX9 was decreased 4 h after ASP treatment compared to non-treated cells. Proteins were extracted from n-MP NHM treated 48 h with ASP and were analyzed by immunoblotting. Concordantly with the RT-PCR results, SOX9 expression was significantly decreased in NHM after treatment with ASP.

SOX9 Induces the Transcription of MITF, DCT and TYR

As SOX9 was up-regulated after UVB exposure, the effects of SOX9 on the activities of MITF, TYR and DCT promoters in B16 melanoma cells were then investigated. Over-expression of SOX9, or treatment with forskolin to a lesser extent, induced a strong activation of the MITF, DCT and TYR promoters. Conversely, SOX9 silencing using SiRNA decreased the MITF, DCT and TYR promoter activities and impaired forskolin induced stimulation. As a control, B16 cells were transfected with pCRE construct (0.3 μg), pCMVbgal (0.05 μg), and an expression vector encoding SOX9 (0.1 μg) or SiRNA of SOX9 (100 nM). Stimulation of a CRE-containing promoter by forskolin was not affected by SOX9 silencing. Finally, in HeLa cells which, in contrast to B16 cells, do not express the protein MITF, over-expression of SOX9 stimulated MITF and DCT promoter activities but not the TYR promoter while forskolin had no effect on the TYR and DCT promoter activity (data not shown). The sum of these data supports the direct activation of the MITF and DCT promoters by SOX9 whereas the TYR promoter seems not to be directly activated by SOX9.

To assess whether SOX9 directly regulates MITF expression, chromatin immunoprecipitation (CHIP) assays were performed on NHM before and 4 h after treatment with forskolin. The CHIP assays clearly showed that SOX9 directly occupies the MITF promoter and that the binding was significantly increased after treatment with forskolin. To determine the relative roles of SOX9 and CREB on the activation of the MITF promoter, the effects of SOX9 over-expression and of stimulation with forskolin on several truncated (in the 5' flanking region) or mutated luciferase constructs of the MITF promoter were studied. B16 cells were transfected with the indicated pMITF constructs (0.3 µg), pCMVbgal (0.05 µg), and an expression vector encoding SOX9 (0.1 µg). The 217 bp construct which has the CRE but lacks all putative SOX9 binding sites showed no significant activation after SOX9 over-expression or forskolin treatment. As previously reported, mutation of the CRE prevents activation of the MITF promoter by forskolin (41). This mutation significantly decreased activation of the MITF promoter after SOX9 over-expression without completely preventing it. Finally, selectively mutating the SOX9 element (−266, −260) showed significant but incomplete decreases in cAMP or SOX9 responsiveness. This incomplete effect could be due to the action of several other putative SOX9 binding sites present on the MITF promoter.

To confirm the role of SOX9 on MITF expression, immunocytochemistry was used to examine the effects of silencing SOX9. NHM were transfected with SOX9 SiRNA and after 24 h the cells were fixed and stained with SOX9 and MITF antibodies. Cells silenced for SOX9 showed a marked decrease in the expression of MITF.

The Effects of SOX9 are Independent of SOX10 Activation

SOX10 has been shown to interact with the MITF and DCT promoters, at least during embryogenesis (29). Thus, some effects of SOX9 could be mediated by SOX10. Therefore, the putative action of SOX9 on SOX10 expression was investigated. After silencing SOX9 in NHM, proteins were extracted 48 h later and analyzed them using Western Blot. The decrease of SOX9 did not affect the level of SOX10 protein (FIG. 8, left panel). SOX9 was then over-expressed in NHM, and extracted proteins 24 h later and then analyzed them using Western Blot. Again, the increase of SOX9 showed no effect on SOX10 protein levels (FIG. 8, right panel). These results show that in NHM, the effects of SOX9 on DCT and MITF targets are not mediated or facilitated through SOX10 regulation.

SOX9 Increases the Expression of Melanogenic Proteins and Enhances Pigmentation

Figure 6A:
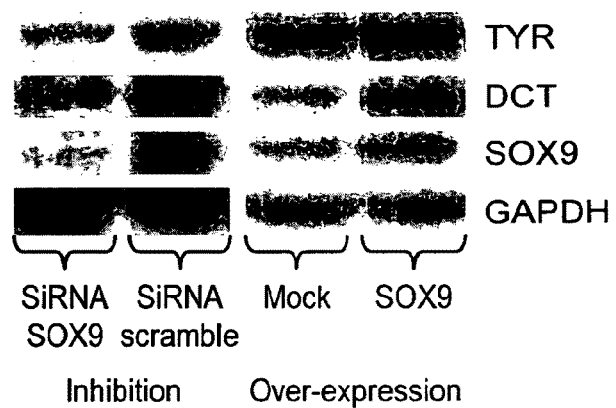
FIG. 6. SOX9 regulates proteins involved in melanogenesis and increases pigmentation of melanocytes. (A) SOX9 was silenced in n-LP NHM using SiRNA for 24 h, then proteins were extracted and analyzed using immunoblotting. Concomitantly with the silencing of SOX9, the expression of DCT and tyrosinase proteins was decreased (left panel). SOX9 was over-expressed for 24 h in n-LP NHM. Again, after extraction, proteins were analyzed using immunoblotting. A parallel increase of DCT and tyrosinase proteins was observed when SOX9 was over-expressed (right panel). (B) n-MP NHM were silenced or over-expressed for SOX9 for 24 and 48 h. After protein extraction, the amount of melanin for each condition was calculated and adjusted against the total protein concentration. The histogram shows quantification of the data with means±SD in 3 independent experiments. Results are expressed as a ratio compared to the basal condition. Except after 24 h of SOX9 silencing, there was a significant decrease of melanin after 48 h of SOX9 silencing and a significant increase after over-expression of SOX9.
Figure 6B:
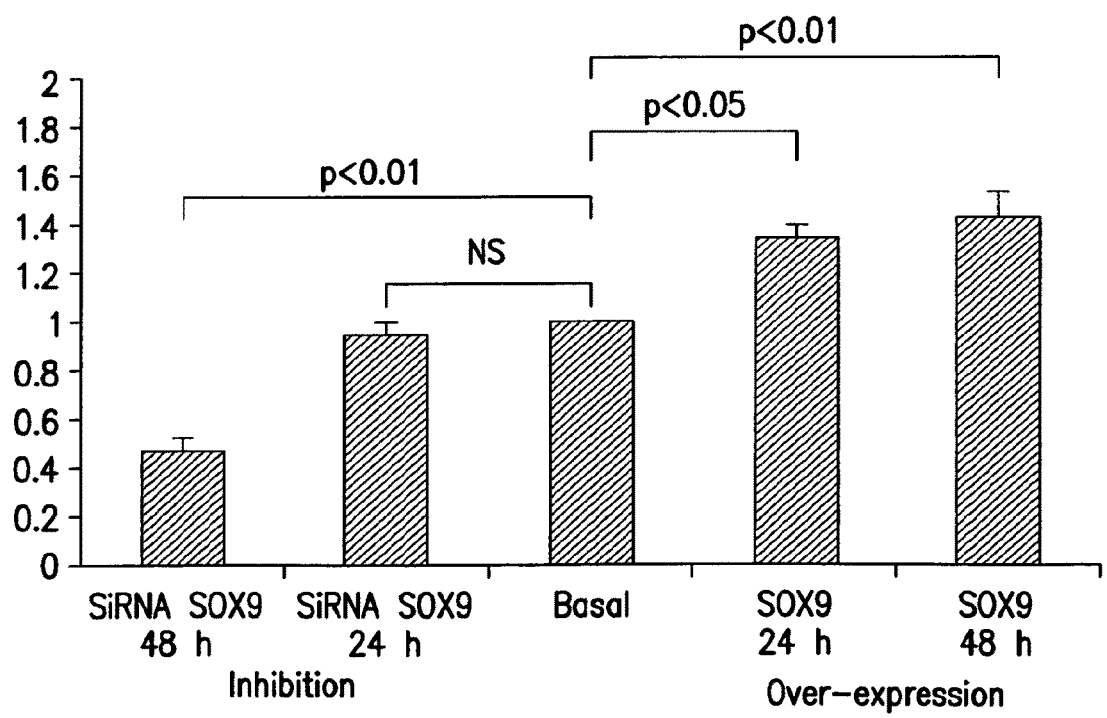

To investigate the action of SOX9 on proteins involved in pigmentation, SOX9 was over-expressed or silenced in n-LP NHM, whereas control n-LP NHM were transfected with SiRNA scramble or over-expression Mock. Proteins were then extracted and analyzed using Western Blot. The expression of DCT and tyrosinase proteins was increased when SOX9 was over-expressed. Concomitantly, when SiRNA was used to silence SOX9, NHM expressed less DCT and tyrosinase proteins compared to the controls (FIG. 6A). As a final target, the amount of melanin produced in n-MP NHM after silencing or over-expressing SOX9 for 24 and 48 h was analysed. The amount of melanin was increased by the over-expression of SOX9 and was decreased by its silencing (FIG. 6B).

Discussion

The present study demonstrates that SOX9 is expressed by NHM in culture as well in adult human skin. The expression of SOX9 is up-regulated in melanocytes after UVB irradiation. As for most of the key players in melanogenesis, the up-regulation of SOX9 is mediated by the cAMP pathway. The transcription factor Usf-1 has also been shown to mediate the UV response in melanocytes by binding the conserved E-Box elements in the tyrosinase promoter (49). Response to UV radiation appears to be tightly regulated and involves several actors, including USF-1 and SOX9, which regulates differentiation in melanocytic cells. The regulation of SOX9 does not affect the expression of SOX10 in neonatal and adult NHM and that the effects of SOX9 on differentiation are not mediated through an increase of SOX10. SOX9 directly binds and regulates the MITF promoter, increases the expression of DCT and tyrosinase, and as a result increases the pigmentation of melanocytic cells. This was corroborated by the results obtained when SOX9 was silenced, showing very slight or no activation of MITF, DCT or TYR promoters after forskolin stimulation. These results emphasize the key roles of both MITF and SOX9 in the melanogenic process in neonatal and adult melanocytes.

A decrease in SOX9 expression occurs after treatment with ASP. SOX9 is up-regulated by αMSH but is down-regulated by ASP in human melanocytes. According to the present results on the effects of SOX9 on MITF, DCT and tyrosinase expression, the down-regulation of SOX9 after ASP treatment could explain, at least in part, the mechanism used by ASP to decrease pigmentation.

The present example discloses the expression of SOX9 at protein and RNA levels in keratinocytes. The previously unrecognized role of SOX9 in pigmentation in neonatal and in adult melanocytes emphasizes the poor understanding of the roles of SOX proteins in adult tissues. In melanocytic cells, SOX9 completes the complex and tightly regulated process leading to the production of melanin by acting at a very upstream level.

Example 3

Mice Over-Expressing SOX9 are Protected Against Melanoma

As shown herein, over-expression of Sox9 in human and mouse melanoma cells strongly decreased their proliferation in cell culture. This study confirms that the decrease of the proliferation rate of cancer cell lines reflects a decrease in its tumorigenicity in vivo. Stable transfection in mouse and human melanoma cells has been established above. Here, mouse melanoma B16/F10 cells are injected into C57B16 mice while human melanoma A375 cells are injected into nude mice. A comparison of wild-type to transfected cells can be made.

The first stage comprises injecting (a) 1×10{6} B16/F10 cells transfected with lentivirus over-expressing Sox9 (total 200 µl) or (b) 1×10{6} B16/F10 cells transfected with lentivirus control into right flank of each C57B16 mouse, SC, needle size 26G1/2. Total 20 mice. Then, 1×10{6} A375 cells transfected with lentivirus over-expressing Sox9 (total 200 µl) or 1×10{6} A375 cells transfected with lentivirus control are injected into right flank of each nude mouse, SC, needle size 26G1/2. Total 20 mice. Tumor size and individual mouse weights are followed from the first day of the experiment and every 4 days thereafter.

After success of the first experiment, lentivirus with SOX9 coding sequence under the control of the MITF promoter is tested. A375 or B16 cells (as used above) are injected via the tail veins of nude and C57B16 mice, respectively. Seven days later, each mouse is be injected IV with 200 µl lentivirus expressing SOX9 driven by MITF. Mice are euthanized at 18 days and pulmonary metastases will be counted as an end point.

REFERENCES

1. Carreira, S., Goodall, J., Aksan, I., La Rocca, S. A., Galibert, M. D., Denat, L., Larue, L., and Goding, C. R. (2005) *Nature* 433(7027), 764-769
2. Wellbrock, C., and Marais, R. (2005) *J Cell Biol* 170(5), 703-708
3. Foster, J. W., Dominguez-Steglich, M. A., Guioli, S., Kowk, G., Weller, P. A., Stevanovic, M., Weissenbach, J., Mansour, S., Young, I. D., Goodfellow, P. N., and et al. (1994) *Nature* 372(6506), 525-530
4. Kwok, C., Weller, P. A., Guioli, S., Foster, J. W., Mansour, S., Zuffardi, O., Punnett, H. H., Dominguez-Steglich, M. A., Brook, J. D., Young, I. D., and et al. (1995) *Am J Hum Genet* 57(5), 1028-1036
5. Akiyama, H., Chaboissier, M. C., Behringer, R. R., Rowitch, D. H., Schedl, A., Epstein, J. A., and de Crombrugghe, B. (2004) *Proc Natl Acad Sci USA* 101(17), 6502-6507
6. Pepicelli, C. V., Kispert, A., Rowitch, D. H., and McMahon, A. P. (1997) *Dev Biol* 192(1), 193-198
7. Pompolo, S., and Harley, V. R. (2001) *Brain Res* 906(1-2), 143-148
8. Afonja, O., Raaka, B. M., Huang, A., Das, S., Zhao, X., Helmer, E., Juste, D., and Samuels, H. H. (2002) *Oncogene* 21(51), 7850-7860
9. Panda, D. K., Miao, D., Lefebvre, V., Hendy., G. N., and Goltzman, D. (2001) *J Biol Chem* 276(44), 41229-41236
10. Larue, L., and Delmas, V. (2006) *Front Biosci* 11, 733-742
11. Ikeda, H., Lethe, B., Lehmann, F., van Baren, N., Baurain, J. F., de Smet, C., Chambost, H., Vitale, M., Moretta, A., Boon, T., and Coulie, P. G. (1997) *Immunity* 6(2), 199-208
12. Epping, M. T., Wang, L., Edel, M. J., Carlee, L., Hernandez, M., and Bernards, R. (2005) *Cell* 122(6), 835-847
13. Malki, S., Nef, S., Notarnicola, C., Thevenet, L., Gasca, S., Mejean, C., Berta, P., Poulat, F., and Boizet-Bonhoure, B. (2005) *Embo J* 24(10), 1798-1809
14. Fitzpatrick, F. A., and Stringfellow, D. A. (1979) *Proc Natl Acad Sci USA* 76(4), 1765-1769
15. Stringfellow, D. A., and Fitzpatrick, F. A. (1979) *Nature* 282(5734), 76-78
16. Bhuyan, B. K., Adams, E. G., Badiner, G. J., Li, L. H., and Barden, K. (1986) *Cancer Res* 46(4 Pt 1), 1688-1693
17. McClay, E. F., Winski, P. J., Jones, J. A., Jennerette, J., 3rd, and Gattoni-Celli, S. (1996) *Cancer Res* 56(17), 3866-3869
18. Akiyama, H., Lyons, J. P., Mori-Akiyama, Y., Yang, X., Zhang, R., Zhang, Z., Deng, J. M., Taketo, M. M., Nakamura, T., Behringer, R. R., McCrea, P. D., and de Crombrugghe, B. (2004) *Genes Dev* 18(9), 1072-1087
19. Jay, P., Berta, P., and Blache, P. (2005) *Cancer Res* 65(6), 2193-2198
20. Lee, J. Y., and Kang, W. H. (2003) *Pigment Cell Res* 16(5), 504-508
21. Drivdahl, R., Haugk, K. H., Sprenger, C. C., Nelson, P. S., Tennant, M. K., and Plymate, S. R. (2004) *Oncogene* 23(26), 4584-4593
22. Virador, V., Matsunaga, N., Matsunaga, J., Valencia, J., Oldham, R. J., Kameyama, K., Peck, G. L., Ferrans, V. J., Vieira, W. D., Abdel-Malek, Z. A., and Hearing, V. J. (2001) *Pigment Cell Res* 14(4), 289-297
23. Bowles, J., Schepers, G., & Koopman, P. (2000) *Dev Biol* 227, 239-255.
24. Mollaaghababa, R. & Pavan, W. J. (2003) *Oncogene* 22, 3024-3034.
25. Pingault, V., Bondurand, N., Kuhlbrodt, K., Goerich, D. E., Prehu, M. O., Puliti, A., Herbarth, B., Hermans-Borgmeyer, I., Legius, E., Matthijs, G., et al. (1998) *Nat Genet* 18, 171-173.
26. Verastegui, C., Bille, K., Ortonne, J. P., & Ballotti, R. (2000) *J Biol Chem* 275, 30757-30760.
27. Potterf, S. B., Mollaaghababa, R., Hou, L., Southard-Smith, E. M., Hornyak, T. J., Arnheiter, H., & Pavan, W. J. (2001) *Dev Biol* 237, 245-257.
28. Ludwig, A., Rehberg, S., & Wegner, M. (2004) *FEBS Lett* 556, 236-244.
29. Jiao, Z., Mollaaghababa, R., Pavan, W. J., Antonellis, A., Green, E. D., & Hornyak, T. J. (2004) *Pigment Cell Res* 17, 352-362.
30. Bell, D. M., Leung, K. K., Wheatley, S. C., Ng, L. J., Zhou, S., Ling, K. W., Sham, M. H., Koopman, P., Tam, P. P., & Cheah, K. S. (1997) *Nat Genet* 16, 174-178.
31. Lefebvre, V., Huang, W., Harley, V. R., Goodfellow, P. N., & de Crombrugghe, B. (1997) *Mol Cell Biol* 17, 2336-2346.
32. Gruber, H. E., Norton, H. J., Ingram, J. A., & Hanley, E. N., Jr. (2005) *Spine* 30, 625-630.
33. Cheung, M. & Briscoe, J. (2003) *Development* 130, 5681-5693.
34. Hedstrand, H., Ekwall, O., Olsson, M. J., Landgren, E., Kemp, E. H., Weetman, A. P., Perheentupa, J., Husebye, E., Gustafsson, J., Betterle, C., et al. (2001) *J Biol Chem* 276, 35390-35395.
35. Huang, W., Zhou, X., Lefebvre, V., & de Crombrugghe, B. (2000) *Mol Cell Biol* 20, 4149-4158.
36. Busca, R. & Ballotti, R. (2000) *Pigment Cell Res* 13, 60-69.
37. Rouzaud, F. & Hearing, V. J. (2005) *Peptides* 26, 1858-1870.
38. Hunt, G. & Thody, A. J. (1995) *J Endocrinol* 147, R1-4.
39. Suzuki, I., Tada, A., Ollmann, M. M., Barsh, G. S., Im, S., Lamoreux, M. L., Hearing, V. J., Nordlund, J. J., & Abdel-Malek, Z. A. (1997) *J Invest Dermatol* 108, 838-842.
40. Sviderskaya, E. V., Hill, S. P., Balachandar, D., Barsh, G. S., & Bennett, D. C. (2001) *Dev Dyn* 221, 373-379.
41. Huber, W. E., Price, E. R., Widlund, H. R., Du, J., Davis, I. J., Wegner, M., & Fisher, D. E. (2003) *J Biol Chem* 278, 45224-45230.
42. Passeron, T., Bahadoran, P., Bertolotto, C., Chiaverini, C., Busca, R., Valony, G., Bille, K., Ortonne, J. P., & Ballotti, R. (2004) *Faseb J* 18, 989-991.
43. Bertolotto, C., Abbe, P., Hemesath, T. J., Bille, K., Fisher, D. E., Ortonne, J. P., & Ballotti, R. (1998) *J Cell Biol* 142, 827-835.
44. Bertolotto, C., Bille, K., Ortonne, J. P., & Ballotti, R. (1996) *J Cell Biol* 134, 747-755.
45. Gaggioli, C., Busca, R., Abbe, P., Ortonne, J. P., & Ballotti, R. (2003) *Pigment Cell Res* 16, 374-382.
46. Cook, A. L., Smith, A. G., Smit, D. J., Leonard, J. H., & Sturm, R. A. (2005) *Exp Cell Res* 308, 222-235.
47. Piera-Velazquez, S., Hawkins, D. F., Whitecavage, M. K., Colter, D. C., Stokes, D. G., & Jimenez, S. A. (2007) *Exp Cell Res* 313, 1069-1079.
48. Levy, C., Khaled, M., & Fisher, D. E. (2006) *Trends Mol Med* 12, 406-414.
49. Galibert, M. D., Carreira, S., & Goding, C. R. (2001) *Embo J* 20, 5022-5031.
50. Bishop, C. E., Whitworth, D. J., Qin, Y., Agoulnik, A. I., Agoulnik, I. U., Harrison, W. R., Behringer, R. R., & Overbeek, P. A. (2000) *Nat Genet* 26, 490-494.
51. Qin, Y., Kong, L. K., Poirier, C., Truong, C., Overbeek, P. A., & Bishop, C. E. (2004) *Hum Mol Genet* 13, 1213-1218.

52. Lee, M., Goodall, J., Verastegui, C., Ballotti, R., & Goding, C. R. (2000) *J Biol Chem* 275, 37978-37983.
53. Yang, C. H., Shen, S. C., Lee, J. C., Wu, P. C., Hsuch, S. F., Lu, C. Y., Meng, C. T., Hong, H. S., & Yang, L. C. (2004) *Gene Ther* 11, 1033-1039.
54. Aberdam, E., Bertolotto, C., Sviderskaya, E. V., de Thillot, V., Hemesath, T. J., Fisher, D. E., Bennett, D. C., Ortonne, J. P., & Ballotti, R. (1998) *J Biol Chem* 273, 19560-19565.
55. Furumura, M., Sakai, C., Potterf, S. B., Vieira, W. D., Barsh, G. S., & Hearing, V. J. (1998) *Proc Natl Acad Sci USA* 95, 7374-7378.
56. Furumura, M., Potterf, S. B., Toyofuku, K., Matsunaga, J., Muller, J., & Hearing, V. J. (2001) *J Biol Chem* 276, 28147-28154.
57. Chen, W., Yang, C. C., Liao, C. Y., Hung, C. L., Tsai, S. J., Chen, K. F., Sheu, H. M., & Zouboulis, C. C. (2006) *J Eur Acad Dermatol Venereol* 20, 846-852.
58. Yasumoto, K., Watabe, H., Valencia, J. C., Kushimoto, T., Kobayashi, T., Appella, E., & Hearing, V. J. (2004) *J Biol Chem* 279, 28330-28338.
59. Larribere, L., Hilmi, C., Khaled, M., Gaggioli, C., Bille, K., Auberger, P., Ortonne, J. P., Ballotti, R., & Bertolotto, C. (2005) *Genes Dev* 19, 1980-1985.
60. Virador, V. M., Kobayashi, N., Matsunaga, J., & Hearing, V. J. (1999) *Anal Biochem* 270, 207-219.
61. Valencia, J. C., Watabe, H., Chi, A., Rouzaud, F., Chen, K. G., Vieira, W. D., Takahashi, K., Yamaguchi, Y., Berens, W., Nagashima, K., et al. (2006) *J Cell Sci* 119, 1080-1091.
62. Mutsuga, N., Shahar, T., Verbalis, J. G., Brownstein, M. J., Xiang, C. C., Bonner, R. F., & Gainer, H. (2004) *J Neurosci* 24, 7174-7185.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating melanoma in a subject by restoring the subject's melanoma cells' sensitivity to retinoic acid (RA), comprising administering to the subject i) prostaglandin D2 (PGD2) or a prostaglandin D2 (PGD2) receptor agonist and ii) retinoic acid (RA) or a retinoic acid receptor (RAR) agonist, wherein the prostaglandin D2 (PGD2) or the prostaglandin D2 (PGD2) receptor agonist is in an amount sufficient to increase SOX9 expression in the subject, thus restoring the subject's melanoma cells' sensitivity to retinoic acid (RA) or the retinoic acid receptor (RAR) agonist, and wherein the retinoic acid (RA) or retinoic acid receptor (RAR) agonist is in an amount sufficient, in combination with the prostaglandin D2 (PGD2) or the prostaglandin D2 (PGD2) receptor agonist, to induce proliferation arrest, differentiation, or apoptosis of melanoma cells, thus treating melanoma in the subject.

2. The method of claim 1 wherein the treating comprises administering to the subject an amount of prostaglandin D2 (PGD2) and retinoic acid (RA) sufficient to treat melanoma.

3. The method of claim 1, wherein the SOX9 decreases PRAME expression.

4. The method of claim 1, wherein the SOX9 increases p21 expression.

5. The method of claim 1, wherein the prostaglandin D2 (PGD2) or the prostaglandin D2 (PGD2) receptor agonist is in a lesser amount than would be administered to the subject to increase SOX9 expression in the subject and to induce proliferation arrest, differentiation, or apoptosis of melanoma cells in the subject in the absence of retinoic acid (RA) or the retinoic acid receptor (RAR) agonist.

6. The method of claim 1, wherein the retinoic acid (RA) or the retinoic acid receptor (RAR) agonist is in a lesser amount than would be administered to the subject to induce proliferation arrest, differentiation, or apoptosis of melanoma cells in the subject in the absence of the prostaglandin D2 (PGD2) or the prostaglandin D2 (PGD2) receptor agonist.

* * * * *